(12) United States Patent
Chiu et al.

(10) Patent No.: US 7,767,435 B2
(45) Date of Patent: Aug. 3, 2010

(54) METHOD AND DEVICE FOR BIOCHEMICAL DETECTION AND ANALYSIS OF SUBCELLULAR COMPARTMENTS FROM A SINGLE CELL

(75) Inventors: Daniel T. Chiu, Seattle, WA (US); Bingyun Sun, Seattle, WA (US); James Patrick Shelby, Bellevue, WA (US); John Scott Edgar, Seattle, WA (US); Gavin Jeffries, Seattle, WA (US); Robert M. Lorenz, Seattle, WA (US); Jason S. Kuo, Seattle, WA (US); Mingyan He, Lynnwood, WA (US); Peter B. Allen, Seattle, WA (US); Sarah Mutch, Seattle, WA (US); Christopher L. Kuyper, Seattle, WA (US); Gina S. Fiorini, Redmond, WA (US); David S. W. Lim, Seattle, WA (US)

(73) Assignee: University of Washington, Seattle, WA (US)

( * ) Notice: Subject to any disclaimer, the term of this patent is extended or adjusted under 35 U.S.C. 154(b) by 1556 days.

(21) Appl. No.: 10/926,656

(22) Filed: Aug. 25, 2004

(65) Prior Publication Data
US 2005/0048581 A1   Mar. 3, 2005

Related U.S. Application Data

(60) Provisional application No. 60/497,874, filed on Aug. 25, 2003.

(51) Int. Cl.
*C12Q 1/68* (2006.01)
*B01L 3/00* (2006.01)
*B01L 3/02* (2006.01)
*B01L 99/00* (2006.01)
*G01N 21/00* (2006.01)
*G01N 15/06* (2006.01)
*C12M 1/36* (2006.01)
*C12M 1/34* (2006.01)
*C12M 3/00* (2006.01)
*C12Q 1/00* (2006.01)

(52) U.S. Cl. ............... 435/286.5; 422/50; 422/55; 422/58; 422/61; 422/68.1; 422/100; 422/101; 435/4; 435/287.1; 435/287.9

(58) Field of Classification Search ............ 422/50, 422/55, 58, 61, 68.1, 100, 101; 435/4, 286.5, 435/287.1, 287.9
See application file for complete search history.

(56) References Cited

U.S. PATENT DOCUMENTS 5,304,487 A * 4/1994 Wilding et al. ............ 435/29

(Continued)

OTHER PUBLICATIONS

Albillos, A. et al., "The exocytotic event in chromaffin cells revealed by patch amperometry," *Nature*, 389: 509-512, Oct. 2, 1997.

(Continued)

*Primary Examiner*—Gailene R Gabel
*Assistant Examiner*—Jacqueline Diramio
(74) *Attorney, Agent, or Firm*—Robert M. Anderson

(57) ABSTRACT

A method and system for performing biochemical detection or analysis on micro- and nano-scale subcellular component within a single biological cell is provided. An integrated platform device and method to perform the biochemical analysis is also provided.

45 Claims, 10 Drawing Sheets

U.S. PATENT DOCUMENTS

| | | | |
|---|---|---|---|
| 6,156,576 A * | 12/2000 | Allbritton et al. | 436/63 |
| 6,511,853 B1 * | 1/2003 | Kopf-Sill et al. | 436/514 |
| 6,969,614 B1 * | 11/2005 | Liotta et al. | 436/177 |
| 7,294,503 B2 * | 11/2007 | Quake et al. | 435/288.5 |
| 2002/0058332 A1 * | 5/2002 | Quake et al. | 435/288.3 |

OTHER PUBLICATIONS

Allen, P. B. et al., "Selective Electroless and Electrolytic Deposition of Metal for Applications in Microfluidics: Fabrication of a Microthermocouple," *Anal. Chem.*, 75: 1578-1583, Apr. 1, 2003.

Anderson, J. R. et al., "Fabrication of Topologically Complex Three-Dimensional Microfluidic Systems in PDMS by Rapid Prototyping," *Anal. Chem.*, 72(14): 3158-3164, Jul. 15, 2000.

Barnes, M. D. et al., "Detection of Single Rhodamine 6G Molecules in Levitated Microdroplets," *Anal. Chem.*, 65: 2360-2365, 1993.

Cannon, D. M. et al., "Quantitative chemical analysis of single cells" *Annu. Rev. Biophys. Biomolec. Struct.*, 29: 239-263, 2000.

Chiu, D. T. et al., "Probing Single Secretory Vesicles with Capillary Electrophoresis," *Science*, 279: 1190-1193, Feb. 20, 1998.

Chiu, D. T. et al., "Chemical Transformations in Individual Ultrasmall Biomimetic Containers," *Science*, 283: 1892-1895, Mar. 19, 1999.

Chiu, D. T., "Micro- and nano-scale chemical analysis of individual sub-cellular compartments," *TrAC-Trend Anal. Chem.*, 22(9): 528-536, 2003.

Cho, S. K. et al., "Creating, Transporting, Cutting, and Merging Liquid Droplets by Electrowetting-Based Actuation for Digital Microfluidic Circuits," *J. Microelectromech. S.*, 12(1): 70-80, Feb. 2003.

Gordon, M. J. et al., "Electrophoretic characterization of dynamic biochemical microenvironments," *J. Am. Chem. Soc.*, 123, 1790-1791, 2001.

He, M. et al., "Concentrating Solutes and Nanoparticles within Individual Aqueous Microdroplets," *Anal. Chem.*, 76(5): 1222-1227, Mar. 1, 2004.

Hochstetler, S. E. et al., "Real-time amperometric measurements of zeptomole quantities of dopamine released from neurons," *Anal. Chem.*, 72: 489-496, Feb. 1, 2000.

Hyden, H. "Isolation and Biochemical Mapping in the Range of 10(-7) to 10(-12)-G of Fresh, Single Mammalian Neurons in Brain .1. Techniques", *Trac-Trends Anal. Chem.*, 14(4): 141-148, 1995.

Hyden, H. "Isolation and Biochemical Mapping in the Range of 10(-7) to 10(-12)-G of Fresh, Single Mammalian Neurons in Brain .2. Some Applications", *Trac-Trends Anal. Chem.*, 14(4): 148-154, 1995.

Jankowski, J. A. et al., "Assaying Single Cells with Capillary Electrophoresis" *Trac-Trends Anal. Chem.*, 14(4): 170-176, 1995.

Kawakatsu, T. et al., "The Effect of the hydrophobicity of microchannels and components in water and oil phases on droplet formation in microchannel water-in-oil emulsification," *Colloid Surface A.*, 179: 29-37, 2001.

Kennedy, R. T. et al., "Microcolumn Separations and the Analysis of Single Cells", *Science*, 246: 57-63, Oct. 6, 1989.

Kuo, J. S. et al., "Electrowetting-Induced Droplet Movement in an Immiscible Medium," *Langmuir*, 19: 250-255, 2003.

Kuyper, C. L. et al., "Optical Trapping: A Versatile Technique for Biomanipulation," *Appl. Spectrosc.*, 56: 300A-312A, 2002.

Li, L. et al., "Single-cell MALDI: a new tool for direct peptide profiling", *Trends Biotechnol.*, 18: 151-160, 2000.

Lillard, S. J. et al., "Monitoring exocytosis and release from individual mast cells by capillary electrophoresis with laser-induced native fluorescence detection," *Anal. Chem.*, 68: 2897-2904, 1996.

Liu, Y. M. et al., "Monitoring cellular release with dynamic channel electrophoresis," *Anal. Chem.*, 71: 28-33, Jan. 1, 1999.

Lowry, O. In Metabolism of the Nervous System; Richter, D.; Pergamon: London, pp. 323-328, 1952.

McDonald, J. C. et al., "Fabrication of microfluidic systems in poly(dimethylsiloxane)," *Electrophoresis*, 21: 27-40, 2000.

Page, J. S. et al., "Single-neuron analysis using CE combined with MALDI MS and radionuclide detection," *Anal. Chem.*, 74: 497-503, Feb. 1, 2002.

Petersson, M. et al., "Sample enrichment in a single levitated droplet for capillary electrophoresis," *S. J. Chrom. B.*, 714: 39-46, 1998.

Ren, H. et al., "Dynamics of electro-wetting droplet transport," *Sensor Actuat. B-Chem.*, 87: 201-206, 2002.

Roddy, T. P. et al., "Imaging of freeze-fractured cells with in situ fluorescence and time-of-flight secondary ion mass spectrometry", *Anal. Chem.*, 74(16): 4011-4019, Aug. 15, 2002.

Santesson, S. et al., "Airborne Cell Analysis," *Anal. Chem.*, 72: 3412-3418, 2000.

Sasaki, K. et al., "Optical trapping of a metal particle and a water droplet by a scanning laser beam," *Appl. Phys. Lett.*, 60(7): 807-809, Feb. 17, 1992.

Schroeder, T. J. et al., "Zones of Exocytotic Release on Bovine Adrenal-Medullary Cells in Culture" *J Biol. Chem.*, 269(25): 17215-17220, Jun. 24, 1994.

Shelby, J. P. et al., "Mapping Fast Flows over Micrometer-Length Scales Using Flow-Tagging Velocimetry and Single-Molecule Detection," *Anal. Chem.*, 75: 1387-1392, 2003.

Sinclair, G. et al., "Interactive application in holographic optical tweezers of a multi-plane Gerchberg-Saxton algorithm for three-dimensional light shaping," *Optics Express*, 12(8): 1665-1670, Apr. 19, 2004.

Song, H. et al., "A Microfluidic System for Controlling Reaction Networks in Time," *Angew. Chem. Int. Edit.*, 42(7): 768-772, 2003.

Thorsen, T. et al., "Dynamic Pattern Formation in a Vesicle-Generating Microfluidic Device," *Phys. Rev. Lett.*, 86(18): 4163-4166, Apr. 30, 2001.

Travis, E. R. et al., "Spatio-temporal resolution of exocytosis from individual cells", *Annu. Rev. Biophys. Biomolec. Struct.*, 27: 77-103, 1998.

Travis, E. R. et al., "Differential quantal release of histamine and 5-hydroxytryptamine from mast cells of vesicular monoamine transporter 2 knockout mice," *Proc. Natl. Acad. Sci. U.S.A.*, 97: 162-167, Jan. 4, 2000.

Welter, E. et al., "Acoustically levitated droplets—a new tool for micro and trace analysis," *Fresenius J. Anal. Chem.*, 357: 345-350, 1997.

Wittig, R. et al., "Vapor-Liquid Equilibria by UNIFAC Group Contribution. 6. Revision and Extension," *Ind. Eng. Chem. Res.*, 42: 183-188, 2003.

Xia, Y. et al., "Soft Lithography," *Angew. Chem. Int. Edit.*, 37: 551-575, 1998.

Yao, H. et al., "Optical Control of Fusion of Microparticles in Solution and Simultaneous Spectrophotometric Measurements," *Anal. Chem.*, 68(23): 4304-4307, 1996.

Yeung, E. S., "Study of single cells by using capillary electrophoresis and native fluorescence detection" *J. Chromatogr. A*, 830: 243-262, 1999.

Yi, C. et al., "Complexometric Determination of Metal Ions by Microscopic Diffusional Titration," *Anal. Chem.*, 68: 1580-1584, 1996.

Zhang, Z. R. et al., "One-dimensional protein analysis of an HT29 human colon adenocarcinoma cell", *Anal. Chem.*, 72: 318-322, 2000.

* cited by examiner

FIG. 14A  FIG. 14B

METHOD AND DEVICE FOR BIOCHEMICAL DETECTION AND ANALYSIS OF SUBCELLULAR COMPARTMENTS FROM A SINGLE CELL

CROSS REFERENCE TO RELATED APPLICATION

This application claims the benefit of U.S. Provisional Application No. 60/497,874, filed Aug. 25, 2003, the entirety of which is incorporated by reference herein.

GOVERNMENT SUPPORT

The invention was made with U.S. Government support under grant Nos. RO1 GM65293 and R21 DA16249 awarded by the National Institutes of Health (NIH), and under grant No. 0135109 awarded by the National Science Foundation (NSF). The Government has certain rights in the invention.

FIELD OF THE INVENTION

This invention relates to a method and a system to perform biochemical detection or analysis on a micro- and nano-scale subcellular component within a single biological cell. The invention further relates to an integrated platform device and method to perform the biochemical analysis.

BACKGROUND OF THE INVENTION

Although powerful imaging systems exist for studying the morphologies of cells and subcellular architectures, no system currently exists to analyze the biochemical compositions of ultrasmall structures at the level of single copies. Despite the power of microscopy in providing nanoscale visual images, there remains a need to obtain chemical information about the subcellular compartments that are being visualized. To obtain information about the localization and function of complex cellular machineries, signaling pathways, and metabolic activities within the cell, a new system capable of providing comprehensive biochemical information about the micro- and nanometer-scale subcellular structures is required.

The primary reason for the lack of techniques in extracting chemical information from micro- and nano-scale subcellular structures lies in the minute amount of samples available for analysis. A typical single organelle may range in diameter from tens of nanometers to a couple micrometers, with a corresponding volume of approximately $6 \times 10^{-20}$ L (e.g., for a 50-nm synaptic vesicle) to approximately $8 \times 10^{-15}$ L (e.g., for a 2-µm mitochondrion). Within a volume of $6 \times 10^{-20}$ L, even at a high concentration of 100 mM, the number of molecules present is only approximately 3600. At this small scale, most proteins would be present as a single copy or a few copies.

At the level of single cells, i.e., the entire contents of a cell rather than an organelle, a number of approaches have been proposed for single-cell microanalysis (Hyden, *Trac-Trends Anal. Chem.*, 14: 141-148, 1995; Hyden, *Trac-Trends Anal. Chem.*, 14: 148-154, 1995; Lowry, O. In METABOLISM OF THE NERVOUS SYSTEM; Richter, D.; Pergamon: London, page 325, 1952; Cannon, et al., *Annu. Rev. Biophys. Biomolec. Struct.*, 29: 239-263, 2000), including voltammetric methods (Travis, et al., *Annu. Rev. Biophys. Biomolec. Struct.*, 27: 77-103, 1998), separation-based strategies (Kennedy, et al., *Science*, 246: 57-63, 1989; Yeung, *J. Chromatogr. A*, 830: 243-262, 1999; Zhang, et al., *Anal. Chem.*, 72: 318-322, 2000; Jankowski, et al., *Trac-Trends Anal. Chem.*, 14: 170-176, 1995), and mass spectrometric techniques (Li, et al., *Trends Biotechnol.*, 18: 151-160, 2000; Roddy, et al., *Anal. Chem.*, 74: 4011-4019, 2002). In comparison with these single-cell studies, the chemical analysis of nanometer scale subcellular compartments presents formidable challenges. The sample volume available for analysis scales as the third power with the diameter of the cellular compartment. Therefore, a typical single mammalian cell with a diameter of approximately 10 µm has a volume of approximately $10^{-12}$ L, which is one thousand times the volume for a large subcellular structure of approximately 1 µm and ten million times the volume for a small synaptic vesicle with a diameter of approximately 50 nm. Most approaches used in single-cell studies are thus inadequate for nano-scale chemical analysis of subcellular structures.

The extremely small volume of the subcellular compartment, combined with a limited number of molecules in a complex mixture, necessitates a system that is both highly sensitive and capable of isolating each component for biochemical quantification and characterization. This invention describes a method and an integrated platform to perform this ultra sensitive analysis.

SUMMARY OF THE INVENTION

Certain aspects of the present invention provide methods, devices, and systems for ultra sensitive biochemical detection and analysis of micro- or nano-scale subcellular structures from a single biological cell. The devices and methods of the present invention provide comprehensive biochemical information on individual subcellular compartments with high spatial resolution. Further aspects of the invention provide methods for isolating subcellular components and molecular components from within a single biological cell using laser-assisted micro- or nano-surgery or using hydrophobic reagents that can permeate a cell membrane of the single biological cell and label a molecular component within a subcellular component of the cell. The device and methods of the present invention can provide spatial information with regard to intracellular localization of molecular components, for example, nucleic acids, proteins, lipids, colloidal entities, small ions, nanoparticles, or other macromolecules, thus providing a powerful complement to many techniques in genomics and in proteomics.

The invention provides a device, method, or system that performs the ultra sensitive biochemical detection and analysis on single biological cells. In one aspect of the device, method, or system, single cells undergo micro- or nano-scale manipulation of their subcellular components (e.g., individual organelles); the subcellular component(s) are encapsulated into droplet form and then are contacted with a chemical reagent to facilitate the downstream detection of molecular components within the subcellular components (e.g., the molecular components are tagged with dyes, quantum dots, or other tangents); then droplet transport and chemical separation occurs (including, but not limited to droplet shuttling, capillary electrophoresis, isoelectric focusing, and gel electrophoresis) followed by an ultra sensitive micro analysis (including, but not limited to laser-induced fluorescence, immunodetection, and matrix-assisted laser desorption/ionization mass spectrometry (MALDI-MS)). In another aspect of the device or system, single cells are contacted with a chemical reagent that can permeate the cell membrane and contact the subcellular component and the molecular components within the subcellular component to facilitate the downstream detection of molecular components within the subcellular component, as described above, by droplet transport, chemical separation and ultrasensitive microanalysis.

The invention provides a method comprising the steps of contacting a subcellular component of a single biological cell with a chemical reactant, separating a molecular component from the subcellular component, and detecting the molecular component of the biological cell. The method further comprises contacting the molecular component with the chemical reactant. The chemical reactant can be a detectable marker, wherein the detectable marker is a reactive dye tag, a fluorescent tag, a non-fluorescent tag, or a contrast agent. The contacting step further comprises encapsulating the subcellular component within a microdroplet. In a further aspect the method comprises isolating the subcellular component from the biological cell. The method further comprises analyzing the molecular component of the biological cell. The contacting step further comprises encapsulating the chemical reactant in a microdroplet, and fusing the chemical reactant microdroplet with the subcellular component microdroplet. The chemical reactant can contact the molecular component. The microdroplet is an aqueous microdroplet, wherein the microdroplet has a volume from about $10^{-9}$ liters to about $10^{-18}$ liters.

In another embodiment, the method comprises permeating a membrane to the chemical reactant. The method further comprises contacting the chemical reactant with the molecular component.

In a further embodiment, the isolating step of the method further comprises using a laser for optical trapping and cellular surgery. The isolating step can use a plurality of lasers. The optical trap comprises an optical vortex trap or an optical gradient trap (optical tweezers).

In a detailed aspect, the subcellular component is an organelle or subcellular compartment. In a further detailed aspect, the molecular component is a single molecule, wherein the molecular component is a colloidal entity, a small ion, a nanoparticle, a nucleic acid, an amino acid, a polynucleotide, a polypeptide, protein, or metabolic precursor or metabolite thereof. The molecular component is a macromolecular assembly, a signaling complex, a lipid- or membrane-containing structure, a carbohydrate-containing structure, a nucleic acid-containing structure, or a polypeptide-containing structure.

The biological cell of the invention comprises an animal cell, a plant cell or a bacterium. Furthermore, the animal cell is a mammalian cell.

When encapsulating the subcellular component within a microdroplet, the method further provides contacting the subcellular component in the aqueous microdroplet with an organic phase, adjusting the starting volume of the organic phase and the period of time of contacting the aqueous microdroplet with the organic phase, and controlling the concentration of the molecular component in the aqueous microdroplet.

The method of the present invention further provides that the detecting step is immuno-labeling, immuno-magnetic labeling, quantum dot attachment, or labeling with a chemically reactive group. The method further provides that the detecting step is single-molecule confocal fluorescence microscopy or mass spectrometry.

The method further provides that the detecting step is immunoassay, enzyme-linked immunosorbant assay (ELISA), Western blot analysis, immunoligand assay, mass spectrometry, electrospray ionization mass spectrometry (ESI-MS), surface-enhanced laser desorption mass spectrometry (SELDI-MS), matrix-assisted laser desorption mass spectrometry (MALDI-MS), secondary ion mass spectrometry (SIMS), radiation-based spectroscopy, laser-induced fluorescence (LIF), two-photon excited fluorescence, surface-enhanced Raman spectroscopy, Fourier transform infrared spectroscopy (FTIR), electric field-based detection, ac impedance spectrometry, voltammetry, electrochemical detection, or conductivity measurement, or other detection techniques known in the art.

The method of the present invention further provides that the separating step is liquid-liquid partition, precipitation, adsorption, chromatography, high-performance liquid chromatography, hydrophobic interaction chromatography, size-exclusion chromatography, protein affinity chromatography, hydroxyapatite chromatography, thiophilic chromatography, hydrophobic charge induction chromatography, immobilized boronic acid ligand chromatography, dye interaction chromatography, metal chelate affinity chromatography, immunoaffinity chromatography, ion-exchange chromatography, capillary electrophoresis, capillary zone electrophoresis, capillary isoelectric focusing, capillary gel electrophoresis, micellar electrokinetic capillary chromatography, or capillary electrochromatography, or other separation techniques known in the art.

The invention provides a method for concentrating a subcellular component in an aqueous microdroplet comprising the steps of contacting the subcellular component in the aqueous microdroplet with an organic phase, and concentrating the subcellular component in the aqueous microdroplet. The method further comprises controlling the concentration of the subcellular component in the aqueous microdroplet by adjusting the starting volume of the organic phase, adjusting the period of time of contacting, or adjusting the composition of the aqueous and organic phases. The method further comprises controlling the concentration of the subcellular component in the aqueous microdroplet using a laser to shrink or expand the volume. In the method of the invention, the organic phase is oil, soybean oil, mineral oil, n-hexadecane, decanol, nonanol, perfluoro-based solution, perfluorononane, perfluorodecane, or acetophenone.

A device of the present invention is provided comprising a substrate to contact a single biological cell, a chemical reactant to contact a subcellular component of the biological cell and a separation microchannel on the substrate to isolate a molecular component from the subcellular component. The device further comprises a detector to identify or analyze the molecular component. The device further comprises a force generator to manipulate the subcellular component.

In a further aspect, the device comprises a laser to isolate a subcellular component from the biological cell, a microfluidic channel on the substrate to receive the subcellular component, and a reactant chamber to generate a microdroplet within the microfluidic channel. In a further aspect the device comprises a first microdroplet generated within the microfluidic channel, said first microdroplet encapsulating the subcellular component, a second microdroplet generated within the microfluidic channel, said second microdroplet encapsulating a chemical reactant, and the force generator to fuse the first microdroplet and the second microdroplet. In a detailed aspect, the laser is an optical vortex trap or an optical gradient trap (optical tweezers). The laser further comprises a plurality of lasers for optical trapping and cell surgery.

The device of the present invention further comprises a reactant droplet chamber to generate a microdroplet with the chemical reactant, the chemical reactant to permeate a membrane of the cell, and a microfluidic channel on the substrate to receive the subcellular component.

The device further comprises the substrate which is a polymeric material, polydimethylsiloxane (PDMS), polymethylmethacrylate (PMMA), polyester (PET), polytetrafluoroethylene (PTFE), polycarbonate, polyurethane, cyclic olefin copolymer, perfluoropolyether, polystyrene, polyvinylchloride, polyethyleneterephthalate glycol, inorganic material, glass, silicon, GaAs, silicon nitride, metals, or a combination thereof.

The device further comprises the chemical reactant which is a detectable marker. The detectable marker can be generated by immuno-labeling, immuno-magnetic labeling, quantum dot attachment or labeling with a chemically reactive group. The detectable marker further comprises a reactive dye tag, a fluorescent tag, a non-fluorescent tag or a contrast agent.

In a further aspect of the device, the microdroplet is an aqueous solution generated in an organic phase. The organic phase is oil, soybean oil, mineral oil, n-hexadecane, decanol, nonanol, perfluoro-based solution, perfluorononane, perfluorodecane, or acetophenone.

The device further provides a force which is mechanical force, electric field force, magnetic field force, hydrodynamic force, surface tension force, interfacial tension force, thermal force, or a combination thereof.

In one aspect of the device of the present invention, the separation microchannel isolates the molecular component by liquid-liquid partition, precipitation, adsorption, chromatography, high-performance liquid chromatography, hydrophobic interaction chromatography, size-exclusion chromatography, protein affinity chromatography, hydroxyapatite chromatography, thiophilic chromatography, hydrophobic charge induction chromatography, immobilized boronic acid ligand chromatography, dye interaction chromatography, metal chelate affinity chromatography, immunoaffinity chromatography, ion-exchange chromatography, capillary electrophoresis, capillary zone electrophoresis, capillary isoelectric focusing, capillary gel electrophoresis, micellar electrokinetic capillary chromatography, or capillary electrochromatography.

In another aspect of the present invention, the detector is a single-molecule confocal fluorescence microscope or a mass spectrometer. The detector further can be an immunoassay, enzyme-linked immunosorbant assay (ELISA), Western blot analysis, immunoligand assay, mass spectrometry, electrospray ionization mass spectrometry (ESI-MS), surface-enhanced laser desorption mass spectrometry (SELDI-MS), matrix-assisted laser desorption mass spectrometry (MALDI-MS), secondary ion mass spectrometry (SIMS), radiation-based spectroscopy, laser-induced fluorescence (LIF), two-photon excited fluorescence, surface-enhanced Raman spectroscopy, Fourier transform infrared spectroscopy (FTIR), electric field-based detection, ac impedance spectrometry, voltammetry, electrochemical detection, or conductivity measurement.

A system of the present invention is provided comprising a substrate to contact a single biological cell, a reactant generation chamber to provide a chemical reactant to contact a subcellular component of the biological cell, and a separation microchannel on the substrate to isolate a molecular component of the subcellular component. The system further comprises a detector to analyze the molecular component. In a further aspect, a microfluidic channel on the substrate to receive the subcellular component.

In a further aspect the system comprises a force generator to manipulate the subcellular component. The force generator can be mechanical force, electric field force, magnetic field force, hydrodynamic force, surface tension force, interfacial tension force, thermal force, or a combination thereof.

In another embodiment, the system comprises the chemical reactant permeating a membrane of the cell. The system further comprises contacting the chemical reactant with the molecular component.

In another embodiment, the system comprises a laser to isolate a subcellular component from the biological cell, a microfluidic channel on the substrate to receive the subcellular component, a first microdroplet generated within the microfluidic channel to encapsulate the subcellular component, a second microdroplet generated within the microfluidic channel to encapsulate a chemical reactant, and the force generator to fuse the first microdroplet and the second microdroplet. In a detailed aspect, the laser is an optical vortex trap or an optical gradient trap/optical tweezers. A plurality of lasers can be used for optical trapping and cell surgery.

In a detailed aspect of the system, the substrate is a polymeric material, polydimethylsiloxane (PDMS), polymethylmethacrylate (PMMA), polyester (PET), polytetrafluoroethylene (PTFE), polycarbonate, polyurethane, cyclic olefin copolymer, perfluoropolyether, polystyrene, polyvinylchloride, polyethyleneterephthalate glycol, inorganic material, glass, silicon, GaAs, silicon nitride, metals, or a combination thereof.

The system of the present invention further comprises a computing device in electrical communication with components of the device. A computing device in electrical communication with the reactant generation chamber controls generation of droplets and size of droplets, and further comprises computer readable instructions to read an input signal from the chamber and generate an output signal to the chamber. A computing device is in electrical communication with the laser to control cell manipulation, and further comprises computer readable instructions to read an input signal from the laser and generate an output signal to the laser. A computing device is in electrical communication with the force generator to control movement of subcellular components and molecular components, and further comprises computer readable instructions to read an input signal from the force generator and an output signal to the force generator. A computing device is in electrical communication with the separation microchannel to isolate the molecular component from the cellular component, and further comprises computer readable instructions to read an input signal from the separation microchannel and an output signal to the separation microchannel. A computing device is in electrical communication with the detector to identify the molecular component, and further comprises computer readable instructions to read an input signal from the detector and an output signal to the detector.

The system further comprises the chemical reactant which is a detectable marker. The detectable marker can be generated by immuno-labeling, immuno-magnetic labeling, quantum dot attachment or labeling with a chemically reactive group. The detectable marker further can be a reactive dye tag, a fluorescent tag, a non-fluorescent tag or a contrast agent.

In a further aspect of the system, the microdroplet is an aqueous solution generated in an organic phase. The organic phase is oil, soybean oil, mineral oil, n-hexadecane, decanol, nonanol, perfluoro-based solution, perfluorononane, perfluorodecane, or acetophenone.

A device for biochemical detection or analysis of a single biological cell of the present invention is provided comprising a substrate for contacting the single biological cell, manipulation means for isolating a subcellular component from the single biological cell, encapsulation means for isolating a chemical reactant from the subcellular component, force means for contacting the subcellular component with the chemical reactant, separation means for isolating a molecular component from the subcellular component, and detecting means for analyzing the molecular component.

BRIEF DESCRIPTION OF THE DRAWINGS

FIGS. 14A and 14B are images showing the size of the soybean oil droplet in DI water remained constant over a period of observation (16 minutes).

DETAILED DESCRIPTION OF ILLUSTRATIVE EMBODIMENTS

The foregoing aspects and many of the attendant advantages of this invention will become more readily appreciated as the same become better understood by reference to the following detailed description, when taken in conjunction with the accompanying drawings.

Figure 1:
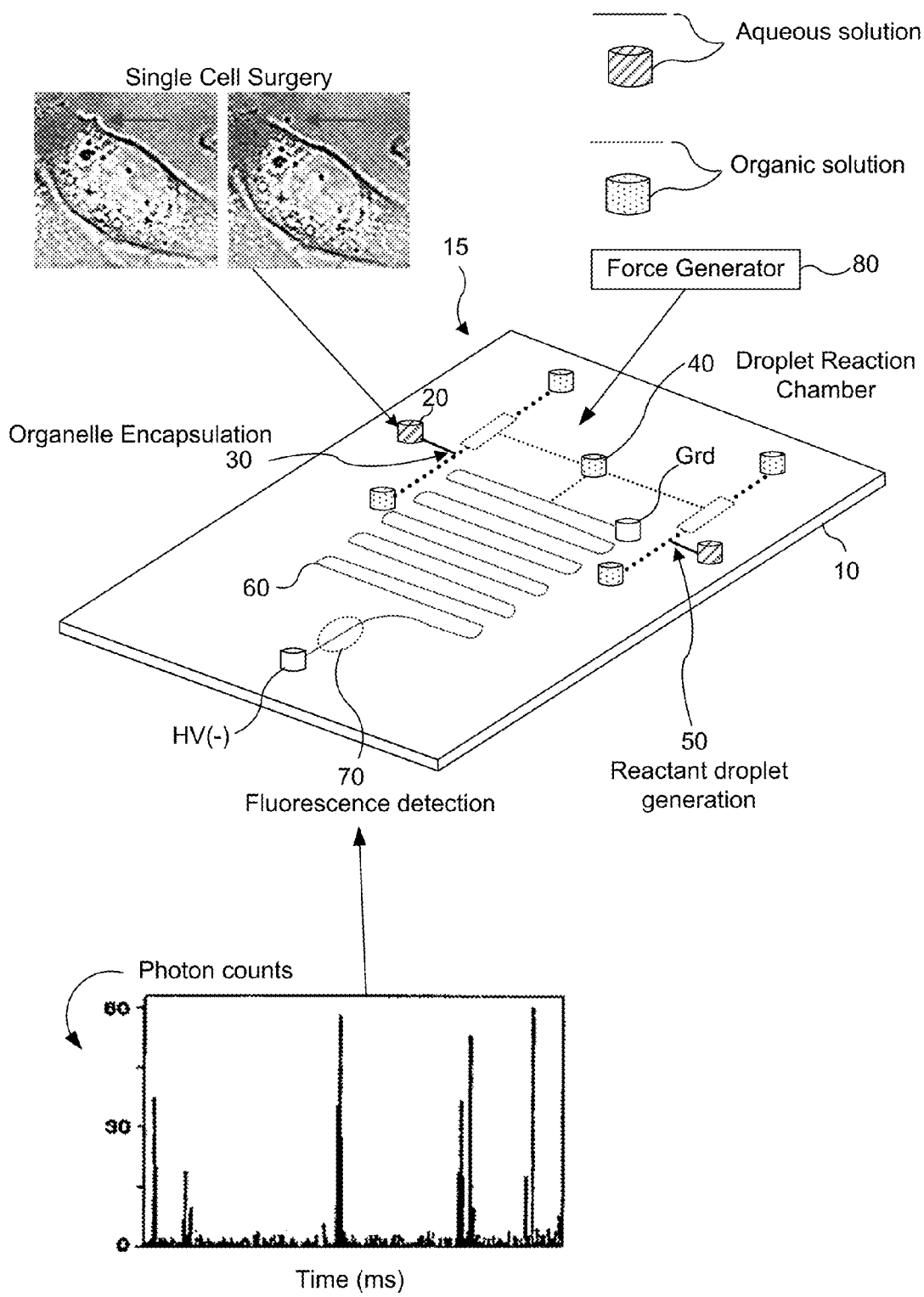
FIG. 1 shows a schematic of the integrated platform device for chemical profiling of a subcellular compartment from a single cell.

FIG. 1 is a schematic of a device 15 showing the elements for analyzing subcellular components and molecular components from a single biological cell. The device 15 has a substrate 10 to contact a single biological cell. A chemical reactant micro- or nano-scale reaction vessel e.g., a microdroplet, is generated at a microdroplet generator 50 to contact a subcellular component of the biological cell. The subcellular component is isolated following micro- or nano-surgery in a surgery chamber 20 and subcellular component (organelle) encapsulation in a microdroplet at a microdroplet generator 30. The chemical reactant microdroplet contacts the subcellular component microdroplet in droplet reaction chamber 40. In an alternative embodiment, the chemical reactant microdroplet contacts an intact single cell. The hydrophobic chemical reactant can permeate the cell membrane and contact the subcellular component and the molecular component within the subcellular component. In either embodiment, the molecular component is separated from the subcellular component in the separation microchannel 60. A force generator 80 moves the microdroplets through the microchannels. The molecular component is isolated by a micro- or nano-scale chemical separation technique (e.g., separation microchannel 60), which includes, but is not limited, to capillary electrophoresis (for fluorescence detection). The separated molecular component is detected by a detector 70 using optically-based or ionization-based sensitive detection, which includes, but is not limited to, laser-induced fluorescence detection or mass spectrometry.

Figure 2:
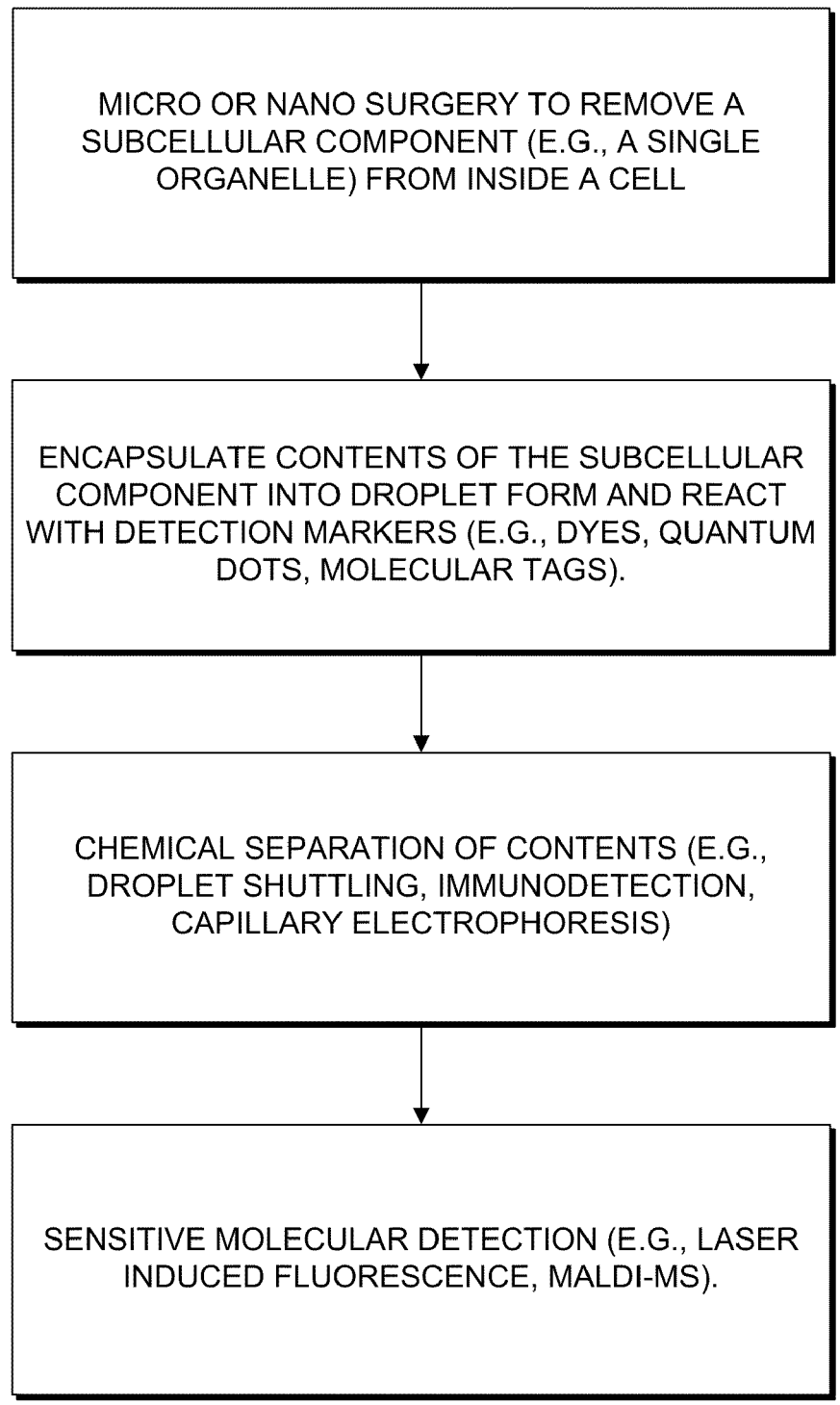
FIG. 2 shows a flow chart of steps in chemical profiling of subcellular compartment from a single cell using microdroplets.

FIG. 2 illustrates the steps in flow chart form for a device for biochemically detecting and analyzing subcellular compartments from a single cell. This device allows the following steps to be performed on substrate 10: (1) identifying the subcellular components of interest, e.g., organelles, using high-resolution microscopy and isolating the subcellular components using laser-based minimally invasive single-cell micro- or nano-surgery in surgery chamber 20; (2) transferring and encapsulating the isolated subcellular component into a micro- or nano-scale reaction vessel, e.g., a microdroplet generated at microdroplet generator 30, while generating another micro- or nano-scale vessel, e.g., a microdroplet at microdroplet generator 50 that contains reactants such as fluorescent dyes or MALDI matrix to modify the content or environment of the subcellular component to suit a downstream detection method; a force generator 80 moves the microdroplets through the microchannels and subsequently combines the contents of the two vessels to carry out a chemical reaction in droplet reaction chamber 40; (3) separating the desired product by a micro- or nano-scale chemical separation technique (e.g., separation microchannel 60), which includes, but is not limited to, capillary electrophoresis (for fluorescence detection); and (4) detecting the separated components by detector 70 using optically-based or ionization-based sensitive detection, which includes, but is not limited to, laser-induced fluorescence detection or mass spectrometry.

Figure 3:
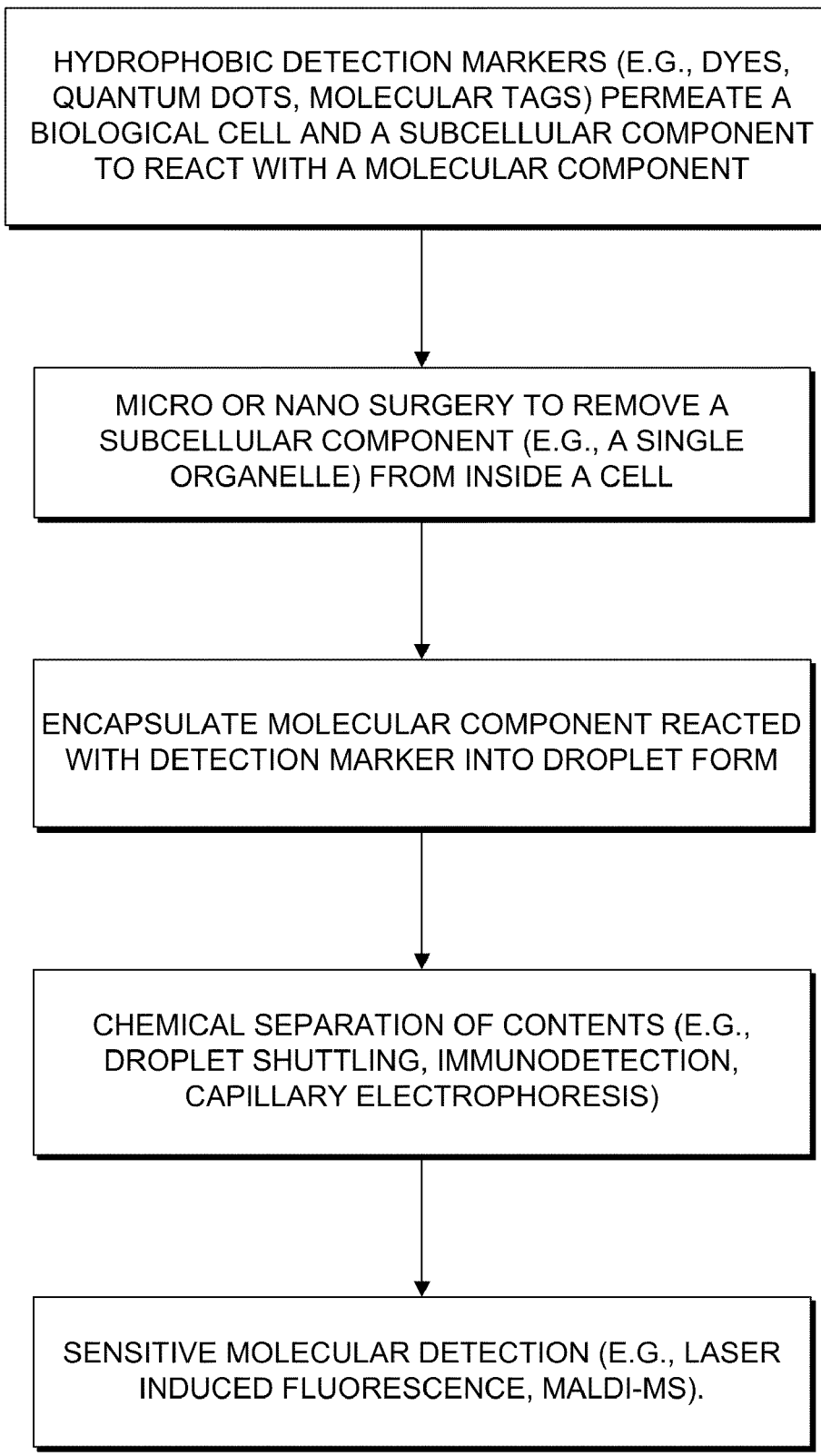
FIG. 3 shows a flow chart of steps in chemical profiling of a subcellular compartment from a single cell using hydrophobic detection markers.

FIG. 3 illustrates the steps in flow chart form for an alternative device for biochemically detecting and analyzing subcellular compartments from a single cell. This device allows the following steps to be performed on a substrate 10: (1) identifying the subcellular components or organelles of interest using high-resolution microscopy and reacting a molecular component within the subcellular component or organelle with a hydrophobic chemical reactant such as fluorescent dyes or MALDI matrix to modify the organelle content or environment to suit downstream detection methods and to label the molecular component. The chemical reactant is generated at the reactant microdroplet generator 50. The chemical reactant is a hydrophobic molecule that can permeate the cell membrane and react with the molecular component within the subcellular component or organelle; (2) transferring and encapsulating the labeled molecular component and/ or isolated subcellular component or organelle into a micro- or nano-scale reaction vessel (e.g., a microdroplet generated at microdroplet generator 30), optionally using laser micro- or nano-surgery; (3) separating the desired product or labeled molecular component by micro- or nano-scale chemical separation technique (e.g., separation microchannel 60), which includes, but is not limited to, capillary electrophoresis (for fluorescence detection); and (4) detecting the separated components by detector 70 using optically-based or ionization-based sensitive detection, which includes, but is not limited to, laser-induced fluorescence detection or mass spectrometry.

Figure 4:
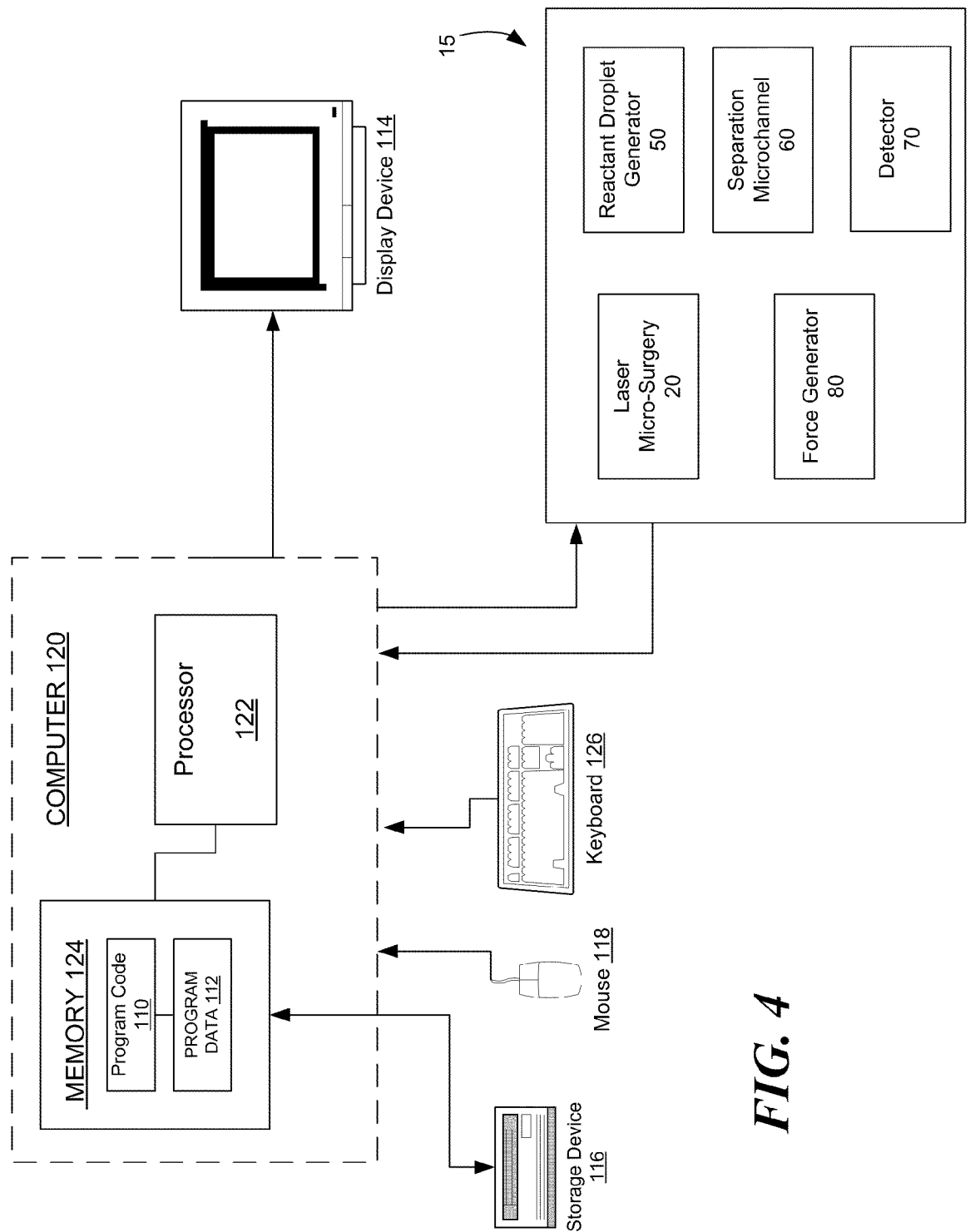
FIG. 4 shows the present invention in the context of flow charts and computer-executable instructions that operate on a computer system to control various steps within a device for biochemical detection or analysis of a single biological cell including single cell manipulation and chemical profiling.

The invention as described herein includes flow charts and computer-executable instructions that operate on a computer system such as the system of FIG. 4 (which provides a block diagram of an exemplary environment in which the invention may be implemented). The computer executable instructions are provided to control various steps including single biological cell manipulation and subsequent chemical profiling within a device for biochemical detection or analysis of the single biological cell. The computer 120 provides computer executable instructions to the device 15 to control various steps in the process including, but not limited to, laser manipulation for micro- or nano-surgery of the single biological cell in surgery chamber 20; generation of microdroplets (at microdroplet generator 50) for encapsulating subcellular components, molecular components, or reactants; control of force generator 80 for manipulating microdroplets; introduction of microdroplets into separation microchannel 60 to isolate molecular components from subcellular components, and a control of detector 70 for the detection of molecular components. The computer provides instructions from the user to the device to control processes including manipulation, detection, and analysis of the cell, subcellular components, and molecular components. The computer receives and analyzes data received from the device to provide the user with data related to biochemical detection and analysis of subcellular components and molecular components within a single cell. Generally, computer-executable instructions are contained in program modules such as programs, objects, data structures and the like that perform particular tasks. Those skilled in the art will appreciate that the invention may be practiced with other computer system configurations, including multi-processor systems, network PCs, minicomputers, mainframe computers and so on. The invention may also be practiced in distributed computing environments where tasks are performed by remote processing devices that are linked through a communications network. FIG. 4 includes a general-purpose computing device, for providing computer-executable instructions to the device 15, in the form of a computer system 120, including a processing unit 122, and a system memory 124. The system memory could include read-only memory (ROM) and/or random access memory (RAM) and contains the program code 110 and data 112 for carrying out the present invention. The system further comprises a storage device 116, such as a magnetic disk drive, optical disk drive, or the like. The storage device 116 and its associated computer-readable media provides a non-volatile storage of computer readable instructions, data structures, program modules and other data for the computer system 120.

A user may enter commands and information into the computer system 120 by way of input devices such as a keyboard 126 and pointing device 118 to control various steps in the process of single biological cell manipulation and subsequent chemical profiling within the device for biochemical detection or analysis of the single biological cell. A display device 114 such as a monitor is connected to the computer system 120 to provide visual indications for user input and output. In addition to the display device 114, computer system 120 may also include other peripheral output devices (not shown), such as a printer.

As used herein, the following terms are provided to assist understanding of the disclosure.

"Biological cell" refers to a cell derived from a plant, animal, fungi, or bacteria, e.g., a mammalian cell, rat cell, mouse cell, or human cell.

"Subcellular component" refers to an organelle or a subcellular compartment of a biological cell, e.g., nucleus, nucleolus, cytoplasm, mitochondria, chloroplast, golgi, synaptic vesicle, vacuole, endoplasmic reticulum, ribosome, or other subcellular structures known in the art.

"Microdroplet" refers to an aqueous solution having a volume of $10^{-9}$ liters or less, $10^{-12}$ liters or less, $10^{-15}$ liters or less, $10^{-18}$ liters or less or $10^{-20}$ liters or less.

"Molecular component" refers to a single molecule, a colloidal entity, a small ion, a nanoparticle, a nucleic acid, an amino acid, a polynucleotide, a polypeptide, or metabolic precursor or metabolite thereof. Molecular component further refers to a macromolecular assembly, a signaling complex, a lipid- or membrane-containing structure, a carbohydrate-containing structure, a nucleic acid-containing structure, or a polypeptide-containing structure.

"Chemical reactant" refers to a compound that reacts with a molecular component within a subcellular component to, label, identify, isolate, and/or quantify the molecular component. In one aspect, the chemical reactant is a hydrophobic compound that is membrane permeable. The chemical reactant enters the subcellular component of the biological cell and reacts with the molecular component.

In another aspect, the chemical reactant is encapsulated in one microdroplet and the subcellular component is encapsulated in a second microdroplet. The chemical reactant microdroplet is fused with the subcellular component microdroplet, thus allowing the chemical reactant to react with or label the molecular component within the subcellular component.

"Vortex trapping" refers to a technique of trapping objects. One drawback of traditional optical tweezers is the fact that the trapped object is localized at the peak of the laser intensity gradient, where the electric field is the highest. This characteristic makes the simultaneous trapping and the fluorescence imaging of a dye-labeled subcellular compartment difficult, owing to two-photon bleaching of the dye by the trapping laser at high powers. To overcome this bleaching problem, an optical vortex trap has been developed where the trapped particle is not trapped at the center of the highest laser intensity, but at a dark point where little laser light is present and trapping occurs because of the ring of laser light that surrounds and confines the trapped object. Traditional optical tweezers rely on the three-dimensional intensity gradient created by focusing the Gaussian ($TEM_{00}$) mode output of a laser. To create a vortex trap, however, the $TEM_{00}$ mode must be converted into an optical vortex, which is a laser beam that has a spiral phase distribution across its intensity profile. Because at the center of the laser beam the phase is undefined, it is a singularity and the intensity must have a zero value. One method to achieve such a conversion is to use a computer generated hologram or spatial light modulator for manipulating the phase profile of the Gaussian laser beam; another approach is to microfabricate a phase plate to directly alter the spatial phase distribution of the laser output. Once converted into an optical vortex beam, the formation of a vortex trap is relatively straightforward and can be achieved using similar optical arrangements as a traditional optical trap.

A further technique for trapping objects utilizes a laser hologram generator to develop hologram patterns to shape the intensity of different portions of a light beam so that several different particles can be simultaneously trapped and individually controlled in three dimensions. An algorithm works quickly enough to control the light beam interactively with a keyboard and mouse. The algorithm repeatedly refines the hologram pattern so that moving, adding and deleting individual light traps does not require recalculating the hologram as a whole. This makes it possible to control the light beam in real-time. Optical tweezers are already used as tools to, for example, hold the ends of a muscle cell and measure its exertion force. More sophisticated optical tweezers exist that offer better three-dimensional control of single cells and subcellular and molecular components within cells. *Optics Express*, Apr. 19, 2004.

"Detectable marker" refers to a moiety that, when attached to a biomolecule, confers detectability upon that biomolecule or another molecule to which the biomolecule binds. Detectable markers include, but are not limited to, reactive dye tag, a fluorescent tag, a non-fluorescent tag, or a contrast agent. Fluorescent moieties are preferred detectable markers according to the invention, but detectable markers also include, for example, isotopes, fluorescent proteins and peptides, enzymes, components of a specific binding pair, chromophores, affinity tags as defined herein, antibodies, colloidal metals (i.e. gold) and quantum dots. Detectable markers may be either directly or indirectly detectable. Directly detectable markers do not require additional reagents or substrates in order to generate detectable signal. Examples include isotopes and fluorophores. Indirectly detectable markers require the presence or action of one or more cofactors or substrates. Examples include enzymes such as β-galactosidase which is detectable by generation of colored reaction products upon cleavage of substrates such as the chromogen X-gal (5-bromo-4-chloro-3-indoyl-β-D-galactopyranoside), horseradish peroxidase which is detectable by generation of a colored reaction product in the presence of the substrate diaminobenzidine and alkaline phosphatase which is detectable by generation of colored reaction product in the presence of nitroblue tetrazolium and 5-bromo-4-chloro-3-indolyl phosphate, and affinity tags.

"Detecting" or "detection" refers to attaching a detectable marker to a molecular component or a subcellular component and measuring the presence of the molecular component or subcellular component by a method of detection, e.g., fluorescence, chemical, affinity tag, radioactivity, immunological, enzymatic, or other methods known in the art.

"Analyzing" or "analysis" refers to subjecting the molecular component or subcellular component to a separating step or a detecting step, including, but not limited to partition, precipitation, adsorption, chromatography, electrophoresis, isoelectric focusing, immunoassay, ELISA, Western blot analysis, immunoligand assay, mass spectrometry, spectroscopy, laser-induced fluorescence, or other techniques known in the art to measure physical properties of a molecular component, e.g., molecular weight, charge, isoelectric point, reactivity with immunological reagents.

Proteins, nucleic acids or other molecules may be labeled with a detectable marker using methods for protein or nucleic acid labeling known in the art. A "detectable marker" refers to a moiety, such as a radioactive isotope or group containing same, or nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). An affinity capture assay may be used.

"Fluorophore" refers to a detectable moiety that, upon absorbing light energy of a given wavelength (the "excitation wavelength"), is excited and emits light of a longer wavelength (the emission wavelength).

"Chromophore" refers to a chemical group capable of selective light absorption resulting in the coloration of compounds or entities containing it.

"Affinity tag" refers to a moiety that is selectively bound by an affinity reagent. The attachment of an affinity tag to a biomolecule confers upon the biomolecule the ability to be selectively bound by the affinity reagent. "Affinity reagent" refers to an agent that selectively binds to an affinity tag. Useful affinity tag pairs include, for example, antibody and antigen, and biotin and avidin or streptavidin. A pair of molecules exhibits "selective binding" if they physically bind one another in the presence of other different molecules to the substantial exclusion of such different molecules.

"Organic phase" refers to a phase immiscible with an aqueous phase, and includes, but is not limited to oils, hydrocarbon oils, higher alcohols, ester oils, or silicone oils. Further examples of an organic phase include, but are not limited to, oil, soybean oil, mineral oil, n-hexadecane, decanol, nonanol, perfluoro-based solution, perfluorononane, perfluorodecane, or acetophenone. Illustrative oils are those of petroleum, animal, vegetable, or synthetic origin. The animal or plant oils are preferably chosen from the group formed by sunflower oil, corn oil, soybean oil, peanut oil, mineral oil, avocado oil, jojoba oil, marrow oil, grapeseed oil, sesame oil, hazelnut oil, fish oils, glyceryl tricaprocaprylate, or plant or animal oils of formula $R_9COOR_{10}$ in which $R_9$ represents a higher fatty acid residue containing from 7 to 29 carbon atoms and $R_{10}$ represents a linear or branched hydrocarbon-based chain containing from 3 to 30 carbon atoms, in particular alkyl or alkenyl, for example purcellin oil or liquid jojoba wax. The mineral oils that may be used in the compositions of the invention are preferably chosen from hydrocarbons, such as hexadecane and liquid paraffin. Examples of fluorine type oil bases are perfluoropolyether, perfluoro decalin and perfluorooctane, perfluorononane, or perfluorodecane.

Examples of hydrocarbon oils are ozokerite, squalane, squalene, ceresin, paraffin, paraffine wax, liquid paraffin, pristane, polyisobutylene, microcrystalline wax and Vaseline; examples of higher fatty acids are lauric acid, myristic acid, palmitic acid, stearic acid, behenic acid, undecylenic acid, oleic acid, linolic acid, linolenic acid, arachidonic acid, eicosapentaenoic acid (EPA), docosa-hexaenoic acid (DHA) isostearic acid and 12-hydroxystearic acid.

Examples of higher alcohols are lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyltetradecynol, cholesterol, phytosterol, POE cholesterol ether, monostearallyl glycerol ether (batyl alcohol) and monooleyl glyceryl ether (celachyl alcohol).

Examples of ester oils are diisobutyl adipate, 2-hexyl decyl adipate, di-2-heptyl undecyl adipate, N-alkylglycol monoisostearate, ceryl isostearate, trimethylolpropane triisostearate, ethylene glycol di-2-ethylhexanoate, cetyl 2-ethyl hexanoate, trimethylolpropane tri-2-ethylhexanoate, pentaerythritol-tetra-2-ethylhexanoate, cetyl octanoate, octyl dodecyl gum ester, olein oleate, octyldodecyl oleate, decyl oleate, neopentylglycol dicaprate, triethyl citrate, 2-ethylhexyl succinate, amyl acetate, ethyl acetate, butyl acetate, isocetyl stearate, butyl stearate, diisopropyl sebacate, di-2- ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, N-lauryl-L-glutamic acid-2-octyldodecyl ester and diisosterallyl malate; examples of glyceride oils are acetoglyceryl, glyceryl trioctanoate, glyceryl triisostearate, glyceryl triisopalmitate, glyceryl monostearate, glyceryl di-2-heptylundecanoate, glyceryl trimyristate and myristic acid isostearic acid diglyceryl ester.

Examples of silicone oils are low viscosity to high viscosity organopolysiloxanes such as dimethylpolysiloxane, methylphenyl polysiloxane, methyl hydrogen polysiloxane and dimethyl siloxane methyl phenyl siloxane copolymer; cyclic siloxanes such as octamethylcyclotetrasiloxane, decamethylcyclopentasiloxane, dodecylmethylcyclohexasiloxane, etramethyltetrahydrogen-cyclotetrasiloxa-ne and tetramethyltetraphenyl-cyclotetra-siloxane; silicone rubber such as high polymer gum dimethylpolysiloxane and gum dimethylsiloxane-methylp-henyl siloxane copolymer, and cyclosiloxane solutions of silicone rubber, trimethylsiloxysilicic acid, cyclosiloxane solutions of trimethylsiloxysilicic acid, higher alkoxy-modified silicones such as stearoxysilicone, higher fatty acid-modified silicone, alkyl-modified silicone, amino-modified silicone and fluorine-modified silicone.

The following provides exemplary embodiments of a method for biochemical detection or analysis of a single biological cell comprising the steps of: isolating a subcellular component from the single biological cell, encapsulating the subcellular component within a microdroplet, contacting a chemical reactant with the subcellular component, separating a molecular component of the subcellular component, and detecting the molecular component within the subcellular component. The following further provides exemplary embodiments for a device and a system which include a substrate, e.g., a single chip, for performing steps of the method.

EXAMPLES

Example 1

On-Chip Integration

Figure 5A:
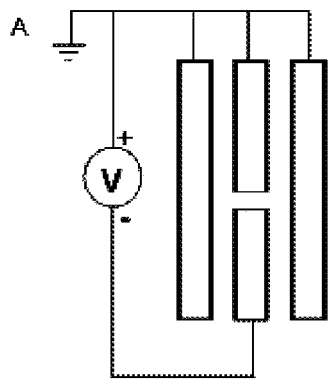
FIG. 5A shows a schematic of the electrode design.
Figure 5B:
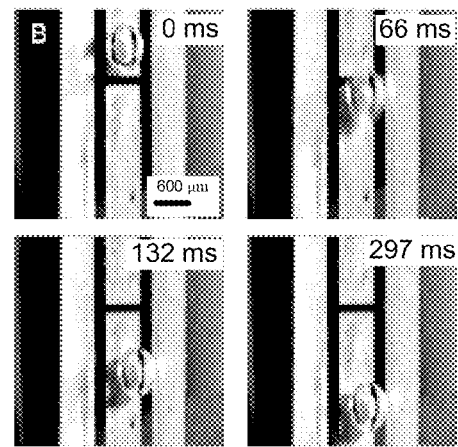
FIG. 5B shows successive video frames showing the manipulation of an aqueous droplet in oil based on the phenomenon of electrowetting.
Figure 6:
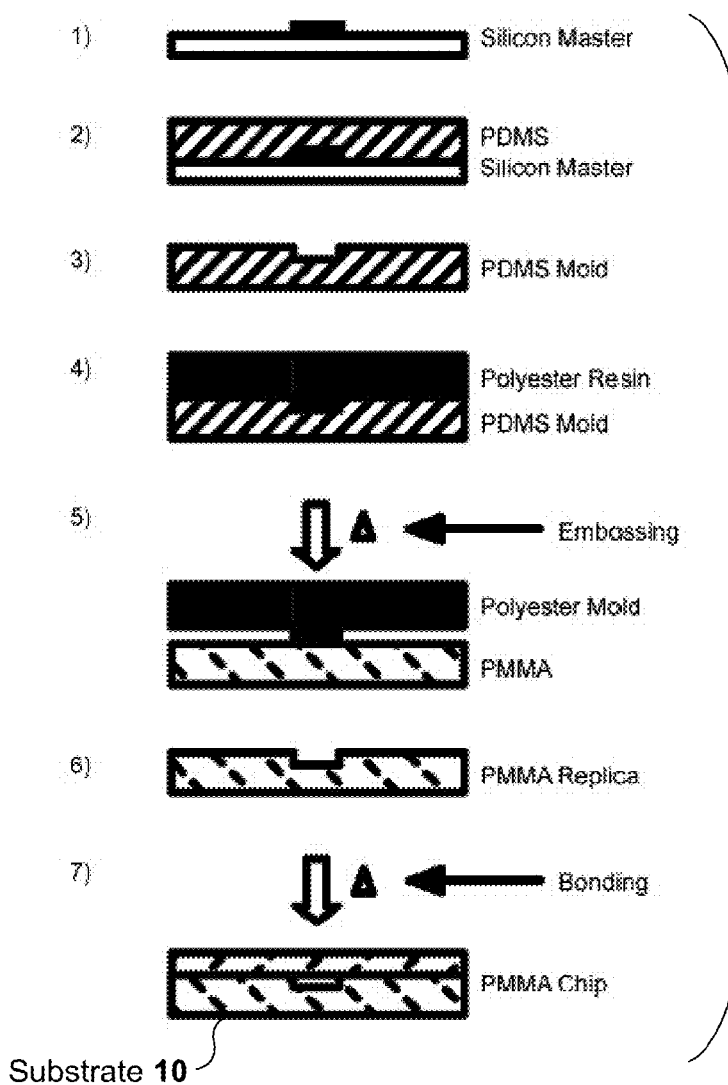
FIG. 6 shows a microfabrication procedure of polymethylmethacrylate (PMMA) chips.

The interface combination of these techniques was performed on a single chip device 15 as illustrated in FIG. 1 (e.g., fabricated in a substrate 10, of a material such as polydimethylsiloxane, polymethylmethacrylate, glass, silicon, polyester, and/or other materials, and combinations thereof) with micro- and nano-fluidic channels, in which single-cell surgery was performed on the substrate 10 in surgery chamber 20, followed by the in-channel droplet generation at the reactant microdroplet generator 50, along with the micro- and/or nano-scale chemical reaction in droplet reaction chamber 40, with each component of the reacted mixture subsequently separated by CE in separation microchannel 60. In the case of laser-induced fluorescence detection, the separated components are detected within the constricted region of the micro- and/or nano-channel using detector 70. In the case of mass spectrometric detection, the separated components or the intact organelles are ionized into the gas phase for mass spectrometric detection. The characterization of each process step is described in the sections that follow. The integration of multiple processes was done by shuttling individual droplet reaction vessels among different regions of the chip-based device using force generator 80, for example, electrowetting (FIG. 5), optical trapping, pressure-driven flow, electrokinetically-driven flow, dielectrophoresis, and/or electrophoresis. An example of the microfabrication method to produce the substrate 10 using polymethylmethacrylate (PMMA) chip construction is described in FIG. 6.

Example 2

Single-Cell Micro- or Nano-Surgery and Micro- or Nano-Scale Chemical Reaction

Figure 7A:
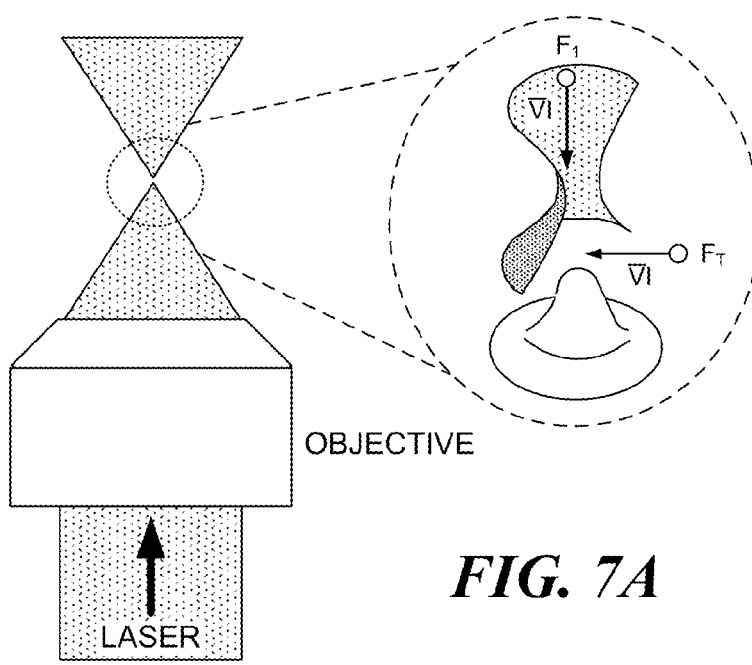
FIG. 7A is an expanded view of the laser focus of a single-beam gradient optical trap.
Figures 7B, 7C, 7D, 7E, 7F, 7G:
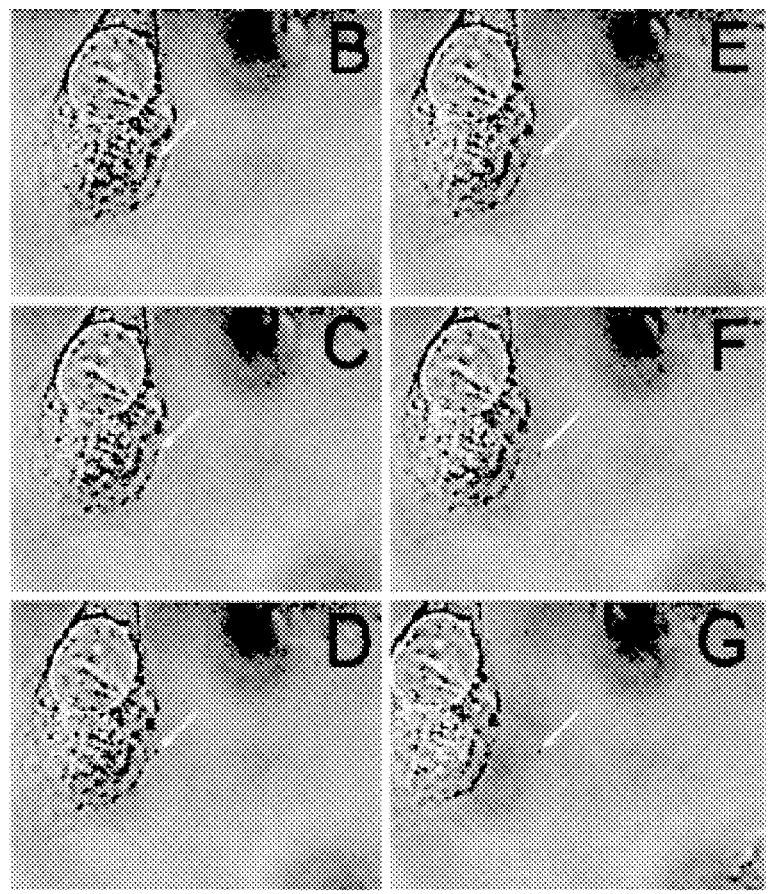
FIGS. 7B-7G show nanosurgery of single cells using a single-beam gradient optical trap.

To isolate single subcellular compartments by single cell nano-surgery in surgery chamber 20, optical trapping was used as a force generator 80 to first manipulate and transport the identified organelles close to the cell membrane (FIG. 7A). Optical trapping has been used in a wide range of applications, from the manipulation of micro- and nano-meter sized particles to single cells and subcellular structures. A single nanometer scale organelle was then moved from the cellular interior to a location adjacent to the membrane surface (FIGS. 7B and 7C, arrow). Once parked at the membrane, the organelle is transported across the cell membrane. A focused ultraviolet (UV) or near infrared (IR) laser (FIGS. 7D-7G), was used to "open" a small nanometer-sized patch on the cell membrane to isolate the organelle from the cell for chemical analysis. Because the cell is a heavily compartmentalized structure, this approach is applicable for the isolation of most intracellular components of interest.

FIGS. 7A-7G shows nanosurgery of single cells in surgery chamber 20. FIG. 7A is a dimensional drawing depicting an expanded view of the laser focus of a single-beam gradient optical trap. The Gaussian laser intensity distribution and the tight focusing provided by the high numerical aperture objective give rise to a traverse force ($F_T$) and a longitudinal force ($F_L$), respectively, for the trapping and manipulating of micro/nano-meter-sized particles. FIGS. 7B-7G are from a video sequence showing the microdissection of a single CHO cells in which a single organelle (arrow) measuring approximately one to two hundred nanometers was selectively isolated from the cell.

Figures 8A, 8B, 8C, 8D:
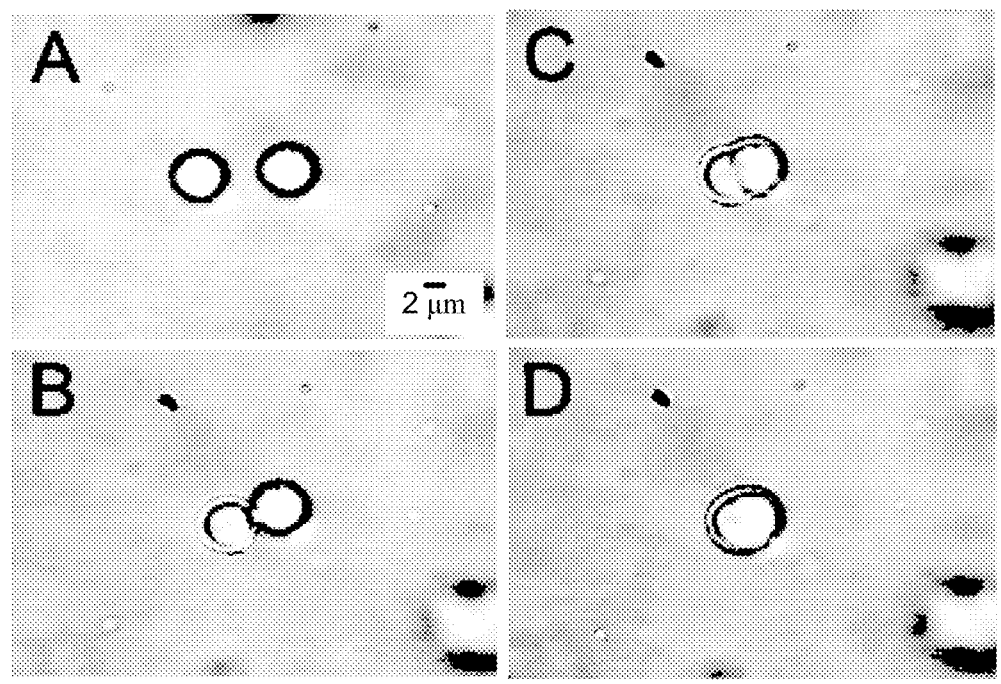
FIGS. 8A-8D show a sequence of video images showing the fusion of two aqueous droplet in oil. The droplets measure approximately 4 µm in diameter, which corresponds to a volume of approximately $2 \times 10^{-13}$ L.

To overcome the detrimental effects of dilution, the molecules to be reacted were confined within a small reaction volume at microdroplet generator 30. This was accomplished by confining the molecules within droplets produced in the micro- and nano-fluidic channels, from which individual droplets ranging from tens of nanometer (comparable to the size of the organelle removed) to several microns in diameter can be generated on demand using pressurized injection of aqueous solution into an immiscible medium or organic phase such as oil. Single droplets were selected and fused, thereby mixing the contents of the different droplets and then allowing chemical reaction to occur in droplet reaction chamber 40. Force generator 80 (an optical trap) was used to force two droplets together. The speed and ease with which droplets can be fused depends on many parameters, such as the size of the droplets and the amount of force by which the droplets are pushed together. In general, small droplets both fuse more slowly and require more force to achieve fusion. The fusion of the droplets (shown in FIGS. 8A-8C) occurred over several seconds. In the case of mass spectrometric analysis of intact organelles, the entire intact organelle may also be encased in suitable matrix for subsequent ionization.

FIGS. 8A-8D show a sequence of video images showing the fusion of two aqueous droplet in oil. The droplets measure approximately 4 μm in diameter, which corresponds to a volume of approximately $2 \times 10^{-13}$ L.

Example 3

Sensitive Detection of Single Fluorescent Molecules

Figure 9:
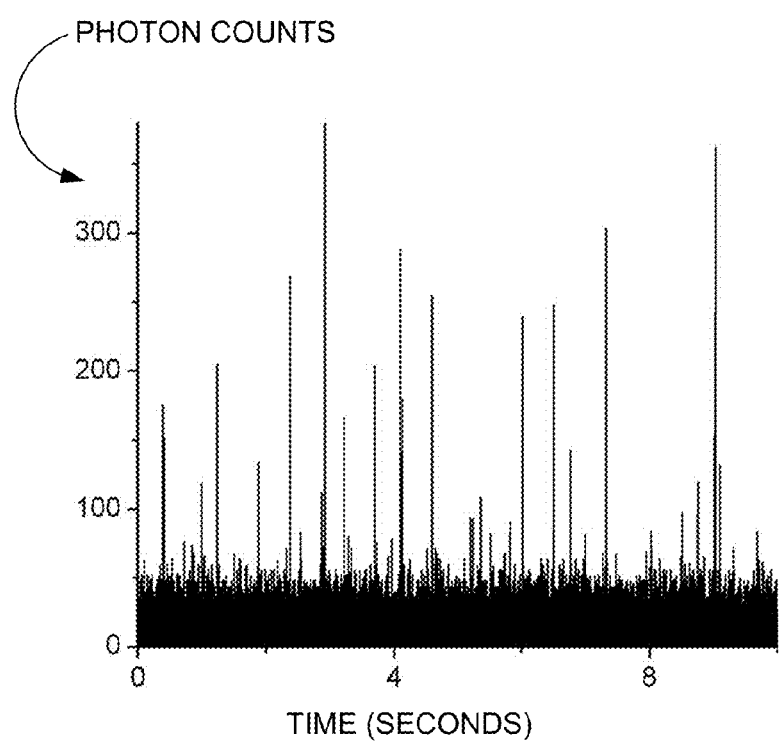
FIG. 9 shows a photon trace demonstrating the detection of single carboxyrhodamine 6G molecule diffusing in solution.
Figures 10A, 10B, 10C, 10D, 10E, 10F, 10G, 10H, 10I, 10J, 10K, 10L:
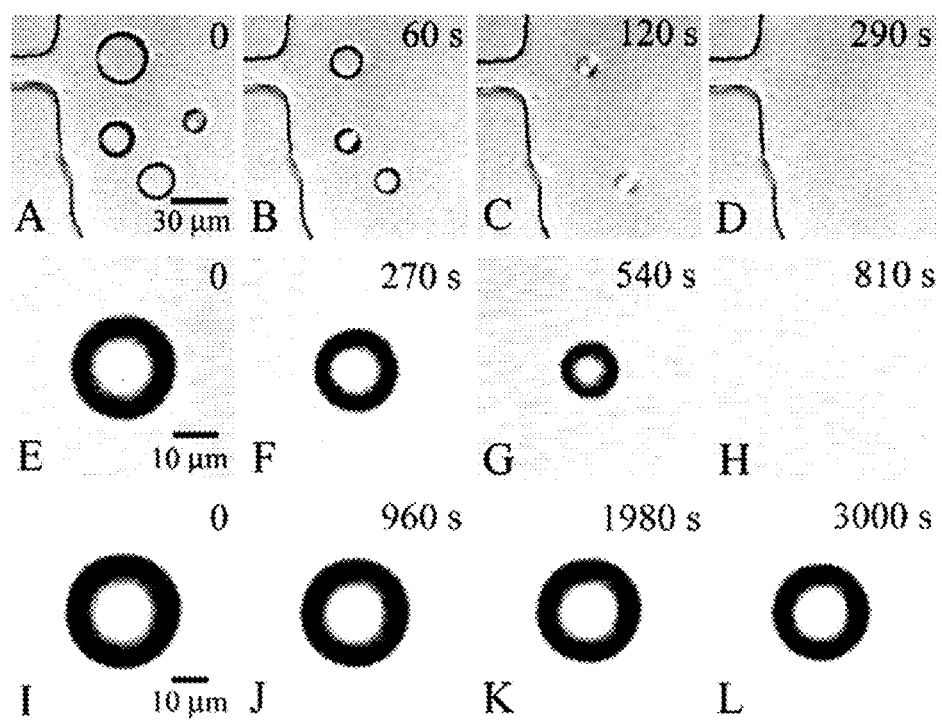
FIGS. 10A-10L show a sequence of micrographs showing the shrinkage of deionized (DI) water droplets over time.

The detection of single fluorescent molecules using detector 70 can be achieved with an excellent signal-to-noise ratio, and has become more facile and routine with improved detectors and optics. The detection volume of a single-molecule confocal fluorescence microscope was defined latitudinally by the laser focus and longitudinally by the pinhole present at the image plane. This far-field method for single-molecule detection shows excellent signal-to-noise ratio at approximately 1-ms photon integration time, which is illustrated in FIG. 9 (which illustrates a photon trace detection of single carboxyrhodamine 6G molecule diffusing in solution, in which each spike signals the presence of a single dye molecule within the probe volume). One criterion employed to achieve such high signal-to-noise ratio is to minimize the laser probe volume by using a diffraction limited laser focus, which is approximately 0.5 μm in diameter and 2 μm in height. This small detection volume ensures low background noise that may be caused by scattering and the presence of impurities. To detect and count every molecule that is present and separated within the capillary, the size of the channel at the detection region must match the size of the laser probe volume Mass spectrometric technique such as MALDI-MS may be used in conjunction with fluorescence detection to provide the structural information of the proteins separated. If the encapsulated reactant in earlier chemical reaction was a MALDI matrix such as sinapinic acid or a-Cyano-4-hydroxycinnamic acid, the product mixture may be directly transported in droplet form to a substrate and for subsequent MALDI-MS analysis.

Example 4

Profiling of Biochemical Components of Cells

This invention can find broad use in any system requiring profiling of biochemical components within single organelles, vesicles, or other micro and/or nano meter-scale features within a cell. Example applications include but are not limited to diagnosing diseases at molecular and cellular level, investigating the effect of pharmacokinetic mechanisms at subcellular level, rapid screening of expression of hereditary diseases, and other biochemical micro-analyses.

The design principles and methods presented can be broadened to include many different types of force generators 80 for cellular manipulation, where the various force generators employ forces including, but not limited to, a mechanical force, an electric field force, a magnetic field force, a hydrodynamic force, a surface tension force, an interfacial tension force, a thermal force, or a combination thereof. Mechanical force refers to a force exerted by, for example, a patch clamp, osmotic pressure-based cellular disruption, shear-based membrane disruption, a micropipette, and microactuators/microrobotics. Electric field force refers to a force exerted by, for example, electroporation, dielectrophoresis, and quadrupole electric field trapping. Magnetic field force refers to a force exerted by, for example, quadrupole magnetic field trapping. Further force generators for cellular manipulation include force generators including a plurality of lasers to achieve optical trapping and membrane surgery; and force generators facilitating chemical reaction techniques such as immuno-labeling, immuno-magnetic labeling, quantum dot attachment; chemical separation techniques such as liquid-liquid partition, precipitation, adsorption, chromatography (which includes but is not limited to high-performance liquid chromatography, hydrophobic interaction chromatography, size-exclusion chromatography, protein affinity chromatography, hydroxyapatite chromatography, thiophilic chromatography, hydrophobic charge induction chromatography, immobilized boronic acid ligand chromatography, dye interaction chromatography, metal chelate affinity chromatography, immunoaffinity chromatography, or ion-exchange chromatography), capillary electrophoresis (CE; which includes but is not limited to capillary zone electrophoresis, capillary isoelectric focusing, capillary gel electrophoresis, micellar electrokinetic capillary chromatography, and capillary electrochromatography), immunoassay (which includes but is not limited to enzyme-linked immunosorbant assay (ELISA), Western blot analysis, and immunoligand assay), other mass spectrometric techniques for the detection of chemical species (including but not limited to electrospray ionization mass spectrometry (ESI-MS), surface-enhanced laser desorption mass spectrometry (SELDI-MS), matrix-assisted laser desorption mass spectrometry (MALDI-MS), Secondary Ion Mass Spectrometry (SIMS), radiation-based spectroscopy (including but not limited to laser-induced fluorescence (LIF), two-photon excited fluorescence, surface-enhanced Raman Spectroscopy, Fourier Transform Infrared Spectroscopy (FTIR)), and electric field-based detection (including but not limited to alternating current impedance spectrometry, voltammetry, electrochemical detection, and conductivity measurement).

The chip can be fabricated on substrates 10 other than described in the example, which can include but is not limited to polymeric material, polydimethylsiloxane (PDMS), polymethylmethacrylate (PMMA), polyester (PET), polytetrafluoroethylene (PTFE), polycarbonate, polyurethane, cyclic olefin copolymer, perfluoropolyether, polystyrene, polyvinylchloride, polyethyleneterephthalate glycol), inorganic materials (glass, silicon, GaAs, silicon nitride), metals, and/or other materials, or combinations thereof.

Example 5

Concentrating Solutes and Nanoparticles within Individual Aqueous Microdroplets The invention provides a method to concentrate solutes and colloidal entities, from small ions and molecules to proteins and nanoparticles, within individual aqueous microdroplets in oil using microdroplet generator 30. The mechanism relies on the entrapment of the solutes within an aqueous microdroplet, while the water molecules from the droplet slowly dissolve into the organic phase. Because the rate of change in concentration scales as the fifth power of the surface-area-to-volume ratio of the droplet, this phenomenon is prominent mostly in the micrometer length scale. The invention provides measurements that quantify the degree of solute entrapment within the microdroplet, and further describes the dynamics of droplet shrinkage and the factors that influence the rate of shrinkage. In addition, the invention explains why this concentration effect does not occur for certain organic microdroplets in aqueous solutions. Monodispersed aqueous droplets ranging from hundreds of micrometers to a few micrometers in diameter can be generated in microfluidic systems (Thorsen, et al., *Phys. Rev. Lett.*, 86: 4163-4166, 2001; Kawakatsu, et al., *Colloid Surface A.*, 179: 29-37, 2001). As discreet containers, these droplets have corresponding volumes of nanoliters ($10^{-9}$ L) to femtoliters ($10^{-15}$ L). The droplets can be used as nanoscale reaction vessels for the chemical manipulations and analysis of subcellular compartments and organelles (e.g., individual mitochondria and single synaptic vesicles) at the level of single copies of components (Chiu, *TrAC-Trend Anal. Chem.,* 22: 528-536, 2003). Aqueous microdroplets possess a number of attractive attributes as nanoreactors: (1) Individual droplets can be manipulated both optically (Sasaki, et al., *Appl. Phys. Lett.,* 60: 807-809, 1992; Yao, et al., *Anal. Chem.,* 68: 4304-4307, 1996; Kuyper, et al., *Appl. Spectrosc.,* 56: 300A-312A, 2002) and electrically (Kuo, et al., *Langmuir,* 19: 250-255, 2003; Cho, et al., *J. Microelectromech. S.,* 12: 70-80, 2003; Ren, et al., *Sensor Actuat. B-Chem.,* 87: 201-206, 2002), (2) Single subcellular compartments can be manipulated and encapsulated into a droplet with high precision and control, (3) Aqueous droplets can be fused easily so their respective contents can be combined and reaction can be initiated (Sasaki, et al., *Appl. Phys. Lett.,* 60: 807-809, 1992; Yao, et al., *Anal. Chem.,* 68: 4304-4307, 1996), and (4) Many droplets can be manipulated, transported, and fused in parallel, which opens the potential for carrying out combinatorial operations and reactions within such droplets. Aqueous droplets represent an important area of research in down-scaled analytical techniques (Yi, et al., *Anal. Chem.,* 68: 1580-1584, 1996; Petersson, et al., *S. J. Chrom. B.,* 714: 39-46, 1998), as reflected in the wide-range of work in the literature on levitating droplets in air (or inert gas) (Petersson, et al., *S. J. Chrom. B.,* 714: 39-46, 1998; Welter, et al., *Fresenius J. Anal. Chem.,* 357: 345-350, 1997; Santesson, et al., *S. Anal. Chem.,* 72: 3412-3418, 2000; Barnes, et al., *Anal. Chem.,* 65: 2360-2365, 1993) and in detecting molecules within such droplets (Santesson, et al., *S. Anal. Chem.,* 72: 3412-3418, 2000; Barnes, et al., *Anal. Chem.,* 65: 2360-2365, 1993).

In the chemical analysis of individual subcellular organelles in which the number of molecules to be analyzed is limited (Chiu, et al., *Science,* 279: 1190-1193, 1998; Chiu, et al., *Science,* 283: 1892-1895, 1999), the ability to concentrate the reactants within the reaction vessel is critical. For example, to react (e.g., fluorescent labeling) the contents of a single synaptic vesicle having a diameter of 50 nm, even if the reaction can be performed in a 1-µm diameter droplet, would still correspond to a 8000-fold dilution as the approximately $6 \times 10^{-20}$ L volume of the synaptic vesicle is combined with the approximately $5 \times 10^{-16}$ L volume of the droplet. Once the biomolecules are tagged with a good fluorophore, however, sensitive single-molecule fluorescence techniques can be used to detect their presence. In such nanoscale bioanalytical applications, therefore, the key to successful analysis lies in the ability to concentrate the extremely limited amount of biological samples in ultrasmall volumes so efficient derivatization of the sample with a good fluorescent tag can occur. To address this challenge, the invention provides a flexible approach to concentrate dissolved species within individual aqueous microdroplets to very high levels. This method exploits the high surface-area-to-volume ratio characteristic of microdroplets and is based on the slow dissolution of water molecules into the organic phase while the solutes are retained within the droplet.

Example 6

Fabrication of Microchannels and In-Channel Generation of Microdroplets

Microchannels were fabricated in polydimethylsiloxane (PDMS) and the fabrication procedure has been described in detail elsewhere (Shelby, et al., *Anal. Chem.,* 75: 1387-1392, 2003; Allen, et al., *Anal. Chem.,* 75: 1578-1583, 2003; McDonald, et al., *Electrophoresis,* 21: 27-40, 2000; Xia, et al., *Angew. Chem. Int. Edit.,* 37: 551-575, 1998; Anderson, et al., *Anal. Chem.,* 72: 3158-3164, 2000). Treatment of the PDMS surface in an oxygen plasma was used both to seal together irreversibly the two surfaces that were brought into contact to form an enclosed microchannel and to render the surfaces hydrophilic. To create microchannels with hydrophobic surfaces, the sealed PDMS channel system was placed in an oven and heated to 120° C. for at least 2 hrs. The height of the microchannels in the experiments was 15 µm, which was determined by the thickness of the spin coated negative photoresist (SU-8). The width of the orifice through which microdroplets were generated was 16 µm. Organic droplets in water were generated at the T-junction of the hydrophilic channel based on the shear-force method (Thorsen, et al., *Phys. Rev. Lett.,* 86: 4163-4166, 2001; Song, et al., *Angew. Chem. Int. Edit.,* 42: 768-772, 2003), while water droplets in oil were created at the orifice of a hydrophobic microchannel as the aqueous phase entered a chamber filled with oil. If the diameter of the droplet is bigger than the height of the microchannel, the droplet is sandwiched between the floor and ceiling of the channel.

Generation of Aqueous Microdroplets in Petri Dish.

This method of generating aqueous microdroplets was faster and easier to use than the in-channel droplet generation method, but it provides little control over the sizes of droplets that were formed. A small petri dish was filled with oil (approximately 15 ml) and a small drop of water (10 µl) was injected into the oil from a micropipette. A plastic pipette was used to stir and break up the drop of water until small droplets with diameters in the range of 1-500 µm were formed. If air bubbles were created during the process, they usually floated to the top surface of the oil and could be removed by suction into the pipette. Because the density of aqueous droplets (e.g., 1.0 g/cm$^3$ for water) is slightly greater than that of the oils used (e.g., 0.92 g/cm$^3$ for soybean oil), the aqueous droplets tend to sediment slowly to the bottom of the petri dish. The free-floating droplets as measured here did not reach the bottom of the dish during the period of observation (<70 minutes).

Visual Observation of Individual Microdroplets.

The droplets were observed at room temperature with an upright microscope (Leitz, Wetzlar, Germany) using a long working distance 20× objective. A high sensitivity camera (Cohu 4910, San Diego, Calif.) was used to monitor changes in the size of droplets as well as for fluorescence imaging. For bright-field imaging, the intensity of the illumination light was set at a very low level to avoid heating the objects that are being visualized. For fluorescence imaging, an excitation filter was used to isolate the blue emission from a Xenon Arc lamp for illumination. To minimize photobleaching of dyes, the blue excitation light was allowed to illuminate the sample for only a couple of seconds during data acquisition.

Materials and Chemicals.

For aqueous droplets in oil, the dispersed phase was pure de-ionized (DI) water or DI water containing one of the following solutes or nanoparticles: sodium chloride (Fisher, Fair Lawn, N.J.), Alexa 488 hydrazide sodium salt (Molecular Probes, Eugene, Oreg.), carbonic anhydrase (CA) from Sigma (St. Louis, Mo.) labeled with fluorescein-5-isothiocyanate (FITC) from Molecular Probes (Eugene, Oreg.), or 27-nm yellow-green fluorescent carboxylate-modified polystyrene spheres (Molecular Probes, Eugene, Oreg.). To dye tag CA with FITC, both a 10 mg/ml CA solution in 0.1M NaHCO$_3$ (Sigma, St. Louis, Mo.) and a 10 mg/ml solution of FITC dye in DMSO (Fisher, Fair Lawn, N.J.) solution were prepared. Then 1-ml of the CA solution was mixed with 100-μl of the FITC solution, and that mixture was incubated for 1 hour at room temperature with continuous stirring. The labeled CA was purified from unreacted FITC by running the reaction mixture through a size-exclusion column (Bio-Rad, Econo-Pac® 10 DG, Hercules, Calif.). The continuous phase for aqueous droplets was soybean oil (Ventura Foods, City of Industry, Calif.), light mineral oil (Fisher, Fair Lawn, N.J.), or n-hexadecane (Sigma, St. Louis, Mo.).

Example 7

Shrinkage of Individual Aqueous Microdroplets

Table 1 summarizes observation of the shrinkage of aqueous microdroplets under different experimental conditions. FIGS. 10A-10D show de-ionized (DI) water droplets in soybean oil in contact with the hydrophobic surface of a PDMS microfluidic system that were generated as the aqueous phase passed through an orifice and entered into a chamber that was filled with the oil. These droplets, with a diameter of 10-30 μm, shrank and dissolved into the continuous phase over a period of approximately 5 minutes at a rate of approximately 402 μm²/min (changes in the surface area over time). Similar behavior was observed for free-floating DI water droplets that were produced outside of microchannels in an oil bath in petri dish, but at a slower rate of shrinkage (approximately 258 μm²/min). FIGS. 10E-10H show the shrinkage and complete dissolution in soybean oil of a DI water droplet with a diameter of 23 μm in contact with polystyrene over a period of 13.5 minutes at a rate of 126 μm²/min. Dissolution of the droplets was observed both for those that were in contact with a hydrophobic substrate (e.g., polystyrene and PDMS) and for those that freely floated in the continuous phase (see Table 1). Droplets that were in contact with substrates generally have a slower rate of shrinkage with the exception for those inside microchannels. FIGS. 10I-10L show that the rate of droplet shrinkage is dramatically reduced in light mineral oil in contact with the polystyrene surface (17 μm²/min), while in n-hexadecane, the rate was even slower at 5.3 μm²/min. In later sections, the factors that influence the rate of droplet shrinkage are described in detail.

TABLE 1

Tabulation of the shrinkage behavior of aqueous microdroplets under different experimental conditions

| Method of droplet generation | Presence of solute/ nano-particle | Organic continuous phase | Substrate | Shrinkage rate, dA/dt (μm²/min) | Residue left |
|---|---|---|---|---|---|
| In petri dish | none | soybean oil | none | 258 | no |
| In petri dish | sodium chloride | soybean oil | none | 298 | yes |
| In petri dish | carbonic anhydrase | soybean oil | none | 254 | yes |
| In petri dish | 27-nm nanoparticle | soybean oil | none | 364 | yes |
| In petri dish | Alexa | soybean oil | polystyrene | 148 | yes |
| In petri dish | none | soybean oil | polystyrene | 126 | no |
| In microchannel | none | soybean oil | PDMS | 402 | no |
| In petri dish | none | light mineral oil | polystyrene | 17 | no |
| In petri dish | none | n-hexadecane | polystyrene | 5.3 | no |

Concentration of Solutes within Aqueous Microdroplets.

Figures 11A, 11B, 11C, 11D, 11E, 11F, 11G, 11H, 11I, 11J, 11K, 11L:
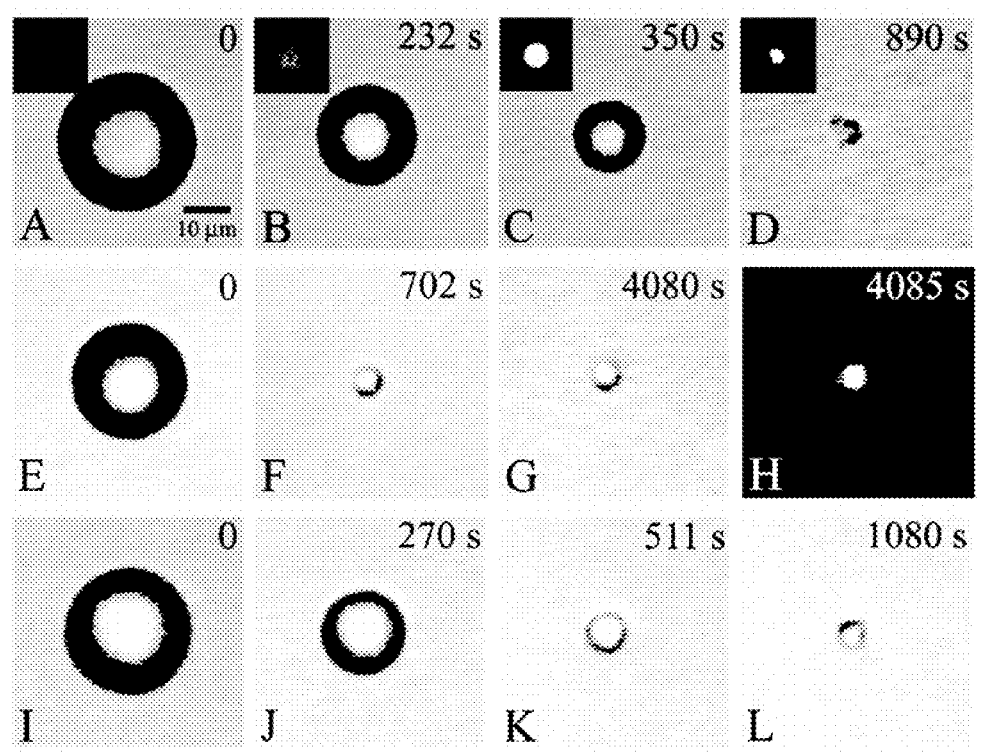
FIGS. 11A-11L show a sequence of micrographs showing the concentration of different types of nanoparticles and solutes within free-floating aqueous microdroplets in soybean oil.

The possibility of exploiting this slow dissolution of water molecules into the organic phase as a platform for concentrating analytes entrapped within a microdroplet was explored. Because most biological molecules of interest (e.g., proteins, peptides, metabolites, amino acids, and ions) contain charges and polar groups, their partition coefficients in most organic phases are negligible. Thus these biological molecules cannot dissolve into oil as the water molecules exit the microdroplet. FIGS. 11A-11L show the concentration of nanoparticles, proteins, and salts within individual water droplets dispersed in soybean oil. The droplet in FIGS. 11A-11D contains 27-nm fluorescent polystyrene beads, which became concentrated as the droplet shrank. The insets are the corresponding fluorescence images showing the expected increase in fluorescence intensity. FIG. 11D shows the resulting aggregate of beads after dissolution of the water molecules from the microdroplet. FIGS. 11E-11H show the concentration of proteins within a microdroplet in which fluorescein-labeled carbonic anhydrase was dissolved. This droplet shrank gradually over 700 seconds or approximately 12 minutes (FIGS. 11E to 11F), after which the size of the droplet remained constant over the period of observation for the next approximately 56 minutes (FIGS. 11F to 11G). FIG. 11H shows the resultant fluorescence image of the concentrated dye-tagged protein. FIGS. 11I-11L show a droplet that contained sodium chloride. The size of the droplet decreased gradually and the shape of the droplet remained spherical for the first 511 seconds or approximately 8.5 minutes (FIGS. 11I to 11K). The droplet then experienced a period (approximately 1 minute) of rapid non-spherical deformation, after which its size and shape remained constant for the remaining 18 minutes as represented by FIG. 11L. The scale bar applies to each of FIGS. 11A-11L.

For DI water droplets that did not contain any solutes, the droplet continued to shrink until it was completely dissolved into the organic phase (FIGS. 10A-10L). For droplets that did contain solutes (FIGS. 11A-11L), the formation of residues has been observed, in which case the size of the droplet initially decreased with time until it has reached its final size (FIGS. 11F to 11G and FIGS. 11K to 11L). Such residues can be spherical (FIG. 11G) or non-spherical (FIG. 11D) depending on the dissolved solutes. Even if the final shape of the residue is spherical, deformation of the droplet was often observed during the last stage of shrinkage. For example, there was non-spherical deformation of the droplet right before the formation of the spherical residue shown in FIG. 11F. Unlike solid-phase extraction, this method concentrates all encapsulated solutes within the droplet rather than a particular solute selectively.

Quantitative Measurements of Solute Entrapment.

Figure 12:
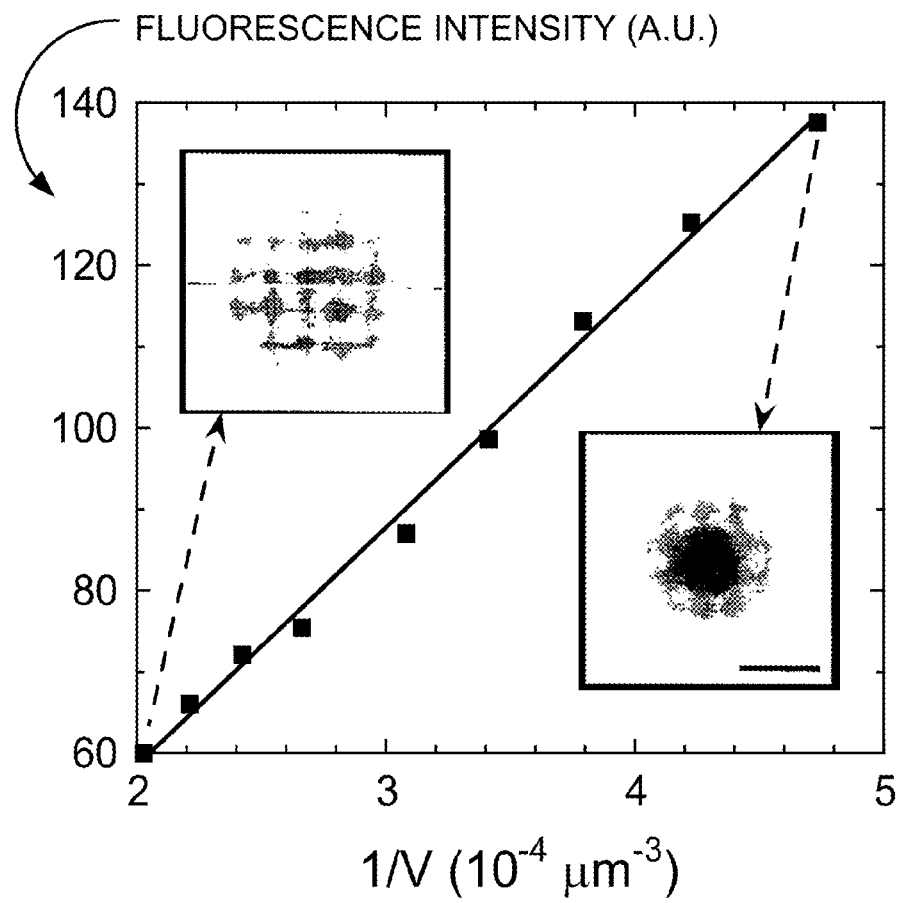
FIG. 12 shows a plot of the measured fluorescence intensity of an aqueous droplet.

To quantify this concentration effect, FIG. 12 plots the increase in fluorescence intensity as the water droplet containing a fluorescent dye, Alexa-488, decreases in volume in a continuous phase of soybean oil. For an ideal non-saturated and non-photobleachable dye, where the depth of focus of the objective lens (e.g., approximately 6 μm) is smaller than the diameter of the droplet, the observed fluorescence intensity should be proportional to the concentration of the dye ($C_s$) in the droplet:

$$F \propto C_s \propto \frac{1}{V} = \frac{3}{4\pi r^3} \quad (1)$$

where F is the fluorescence intensity, and V and r are the volume and the radius of the droplet, respectively. The fluorescence intensity was obtained from a spatial average of the digitized gray-value measurements, in which the intensity from the inner two thirds of the droplet was used to avoid any blurring effects caused by the boundary of the droplet. The fluorescence intensity was calculated by subtracting the background noise ($G_0$) from the measured average gray-value intensity (G).

FIG. 12 shows a plot of the measured fluorescence intensity of an aqueous droplet, which contained the fluorescent dye Alexa-488, increased linearly with the reciprocal of the volume of the droplet. The solid line is a linear fit. The insets show the corresponding fluorescence images of the droplet at the indicated time points. The scale bar represents 10 μm and applies to both insets. FIG. 12 shows a linear fit between the observed increase in the fluorescence intensity versus the corresponding decrease in droplet volume. The approximately 2.3 times increase in the fluorescence intensity matches perfectly the approximately 2.3 times decrease in volume, which indicates that the fluorescent dye Alexa-488 was concentrated gradually inside the aqueous droplet and did not diffuse into the organic phase as anticipated. As the droplet continued to shrink, however, a maximum was observed, followed by a gradual decrease in the observed fluorescence intensity. The observed intensity plateaued because as the diameter of the droplet becomes smaller than the depth of focus, Equation (1) is no longer valid as the number of fluorescent molecules within the probe volume does not change with increases in concentration. The eventual decrease in fluorescence intensity suggests that the fluorescent dye Alexa-488 may self-quench at high concentrations. The key point is that molecules of the fluorescent dye Alexa-488 (and presumably other charged molecules, such as amino acids and proteins) were fully retained in the droplet and could be quantitatively concentrated as the droplet shrank Dynamics of Shrinkage of Aqueous Microdroplets.

Figures 13A, 13B:
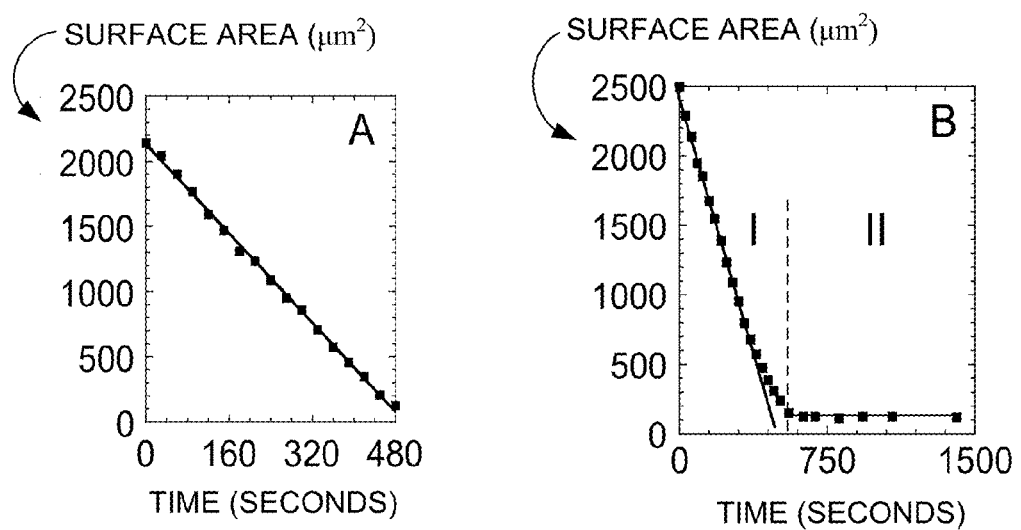
FIG. 13A shows the surface area of a free-floating DI water droplet in soybean oil decreased linearly with time.
FIG. 13B shows that the shrinkage of water droplets containing sodium chloride in soybean oil can be divided into two time regimes.

FIG. 13A shows that the surface area of a pure water droplet in soybean oil decreased linearly with the increase of time. However, for a water droplet that contained sodium chloride (FIG. 13B), two regimes in the droplet shrinkage were observed. In Regime I, the surface area of the droplet decreased linearly with the increase of time, with non-linear deviation around the end of this regime. In Regime II, the surface area of the 'droplet' or residue remained constant. "Shrinkage rate" was defined as the slope in Regime I. For aqueous droplets that contained dye-labeled proteins or fluorescent molecules, the relationship between surface area versus time is similar to the one shown in FIG. 13B, except that the shrinkage rates and non-linear deviations vary. For aqueous droplets containing nanoparticles, however, no non-linear deviation was observed at the end of Regime I. Solid lines are linear fits. In the following, a model is presented that describes the dynamics of droplet shrinkage.

For a pure water droplet in oil (suppose oil is stagnant), the diffusion rate ($N_w$, in unit of mol s$^{-1}$m$^{-2}$) of water molecules from the droplet to the surrounding oil is: (Geankoplis, C. J., *Transport Processes And Unit Operations*; Prentice Hall PTR: Engelwood Cliffs, N.J., 1993)

$$N_w = \frac{D_{wo}}{r}(C_w - C_{w\text{-}ref}) \quad (2)$$

where $D_{wo}$ is the diffusivity of water in oil, $C_w$ and $C_{w\text{-}ref}$ are the concentrations of water on the surface of the droplet and at a reference point far away from the droplet, respectively.

The diffusion rate can be rewritten as:

$$N_w = -\frac{d(m_w/M_w)}{A\,dt} \quad (3)$$
$$= -\frac{\rho_w}{M_w A}\frac{dV}{dt} = -\frac{\rho_w}{M_w}\frac{dr}{dt}$$

where $m_w$ is the mass of water in the aqueous droplet, $M_w$ and $\rho_w$ are the molecular weight and density of water, respectively, A is the surface area of the droplet, and t is time.

Suppose $C_{w\text{-}ref}$ does not change with time (e.g., at steady state), from Equation (2) and (3), one gets:

$$\frac{dr}{dt} = -\frac{M_w D_{wo}(C_w - C_{w\text{-}ref})}{\rho_w r} \quad (4)$$
$$\frac{dA}{dt} = -\frac{8\pi M_w D_{wo}(C_w - C_{w\text{-}ref})}{\rho_w} = -k_1$$
$$A = -k_1 t + k_2$$

where $k_1$ and $k_2$ are constants. $k_1$ is what is called the 'shrinkage rate'. Equation (4) shows that the surface area of the water droplet in oil decreases linearly with the increase of time, which is similar to the evaporation of water drops in stagnant dry air (Ranz, et al., *Chem. Eng. Prog.*, 48: 173-180, 1952; Ranz, et al., *Chem. Eng. Prog.*, 48: 141-146, 1952).

From the experimental results, Equation (4) is valid for a free-floating water droplet with Brownian motion and sedimentation (FIG. 13A). In addition, Equation (4) can be considered to be valid for an aqueous droplet with dilute solutes (FIG. 13B Regime I). However, non-linear deviations can be expected for a concentrated droplet, as shown in FIG. 13B close to the end of Regime I. Such deviations are caused by the changes of relative concentration of water at the droplet surface.

Because the surface-to-volume ratio (SV) scales as 1/r with the radius of a spherical droplet, the rate of change in solute concentration ($dC_s/dt$) as a function of surface-to-volume ratio for an aqueous droplet containing dilute solute is:

$$\frac{dC_s}{dt} \propto \frac{1}{r^4}\frac{dr}{dt} \propto \frac{1}{r^5} \propto (SV)^5 \quad (5)$$

whereas the rate of change of surface-to-volume ratio (d(SV)/dt) versus the radius of the droplet is $1/r^3$.

Equation (5) indicates that the rate of change in concentration of the solute inside a dilute aqueous droplet scales as the $5^{th}$ power of its surface-to-volume ratio. Because of this strong dependence on the surface-to-volume ratio of the droplet, the concentration effect cannot be readily observed within short time scales at the macroscale where surface-to-volume ratio is low. In the micro and nano-meter length scale, however, this effect becomes noticeable and practical to implement. The size range of the droplets studied here (from tens of micrometers to a few micrometers) is comparable to or slightly larger than the size of a typical mammalian cell, which makes this range of droplet sizes suitable for applications in single-cell and subcellular analysis.

Influence of the Organic Phase on Shrinkage of Aqueous Droplets.

One important factor that affects droplet shrinkage lies in the organic phase, as would be expected based on the differences in the solubility of water in different types of oil or organic solvents. Soybean oil is composed of triacylglycerols derived from glycerol and carboxylic acids, of which the main components are linoleic acid (50%-60%), oleic acid (22%-34%), and palmitic acid (7%-11%). Because of the presence of the ester groups, a small amount (0.3 volume % as calculated in later sections) of water can be dissolved into soybean oil (FIGS. 10A-10H). In contrast, light mineral oil is a mixture of hydrocarbons mainly composed of alkanes in the range of fifteen carbons through fifty carbons, which makes the dissolution of water molecules into it highly unfavorable (FIGS. 10I-10L). The slowness of droplet evaporation in a suitable organic phase (over minutes) may prove to be an important advantage as it offers more precise control over the evaporation process. By tuning the composition of the organic phase and by placing individual droplets in different organic environments created within microfluidic systems, the rate and extent of the droplet shrinkage can be exquisitely controlled.

Effects of Concentration Gradients on the Rate of Droplet Shrinkage.

Two observations were made on the rate of droplet shrinkage (Table 1): (1) outside of microchannels, a free-floating droplet generally shrinks faster than a droplet in contact with a substrate, and (2) inside microchannels, a droplet usually shrinks at a significantly faster rate in comparison with that outside of channels. For example, the shrinkage rate of a freely floating DI water droplet was 258 $\mu m^2$/min, while inside microchannels, despite the droplets were in contact with a hydrophobic substrate, the rate of shrinkage was 402 $\mu m^2$/min.

These differences in the rates of shrinkage were caused by the differences in the concentration gradients of water surrounding the droplet. If the concentration of water reaches the maximum saturation level in the bulk oil, there is no concentration gradient and the rate of droplet shrinkage would be zero. In this experiment, the water-oil volume ratio is approximately 0.07%, which is much smaller than the saturation concentration for water in soybean oil of 0.3%.

For an aqueous droplet in contact with a hydrophobic substrate, the surrounding oil does not move. In contrast, for a free-floating droplet, which undergoes Brownian motion and sedimentation, the surrounding oil is less saturated with water because it is frequently replaced. Thus, $C_{w-ref}$ (with the same distance between the droplet and the reference point) of a free-floating droplet is smaller in Eq (4) than for an immobile droplet. Therefore, a droplet in contact with a surface would have a smaller rate of dissolution. Despite the presence of surface contacts, an aqueous droplet localized inside a microchannel has a much faster rate of shrinkage over those dispersed in bulk fluid. This discrepancy can be explained by the presence of siphoning in microchannels, which leads to oil flow and thus efficient mass transfer of water away from the droplet and into oil.

Behavior of Organic Microdroplets in Water.

Figure 14C:
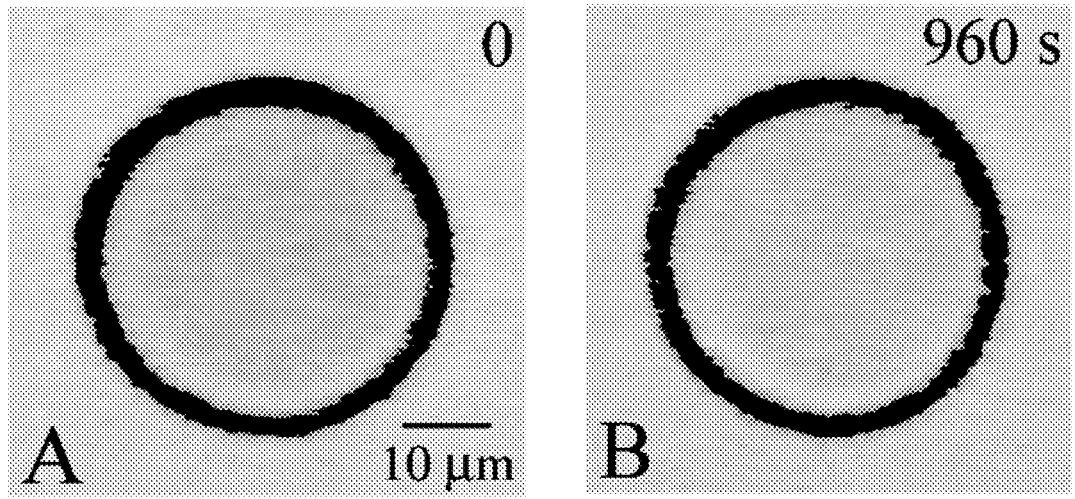
FIG. 14C shows the Gibbs free energy of mixing of soybean oil and water at 25° C.
Figure 14C:
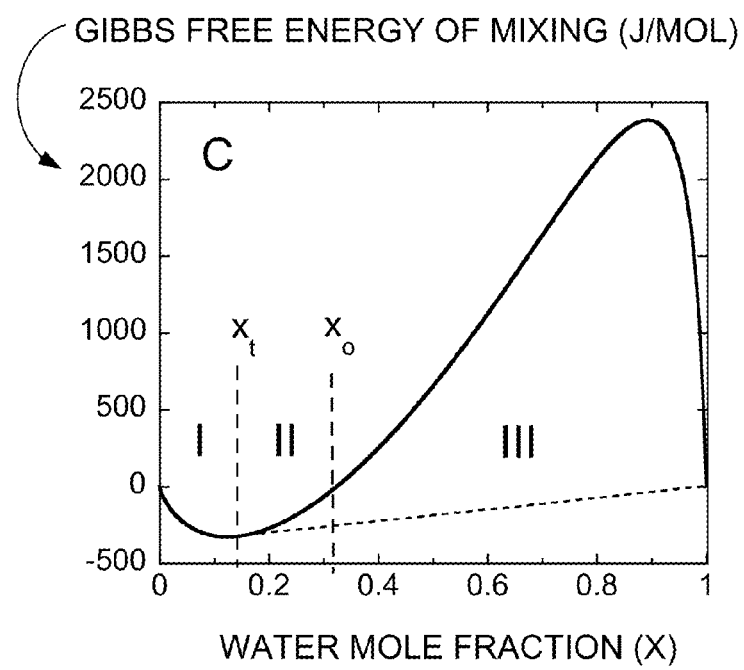

In contrast to aqueous droplets in soybean oil, noticeable shrinkage of a droplet of soybean oil in water was not observed, as shown in FIGS. 14A-14C. FIGS. 14A and 14B are images showing the size of the soybean oil droplet in DI water remained constant over a period of observation (16 minutes). FIG. 14C shows the Gibbs free energy of mixing of soybean oil and water at 25° C. as a function of the water mole fraction, x, as calculated by UNIFAC. $x_t$ is associated with the tangent point on the curve, and $x_o$ is the water mole fraction above which the Gibbs free energy of mixing becomes positive. The water-oil solution is stable in Regime I, metastable in Regime II, and unstable in Regime III in which phase splitting is guaranteed. This asymmetric behavior suggests that although a finite amount of water can dissolve in soybean oil, the vice versa is thermodynamically unfavorable. To explain this asymmetry, the Gibbs free energy of mixing ($g^{mix}$) was calculated on a per mole basis for water and soybean oil using the universal functional activity coefficient (UNIFAC) method (Fredenslund, et al., Vapor-Liquid Equilibria Using UNIFAC: a Group Contribution Method; Elsevier: N.Y., 1977). In UNIFAC, solutions are treated as mixtures not of molecules, but of functional groups, out of which the original molecules can be reconstructed. The relative volumes, areas, and interaction parameters of sixty-four main groups and twice as many sub-groups have been published (Wittig, et al., *Ind. Eng. Chem. Res.*, 42: 183-188, 2003). UNIFAC directly yields the excess activity coefficients of the compounds in the solution, which are then used to calculate the excess Gibbs free energy of mixing. The actual Gibbs free energy of mixing, $g^{mix}$, was obtained by adding this excess Gibbs free energy of mixing to the ideal Gibbs free energy of mixing. A combination of triacylglycerols with 60% linoleic acid, 30% oleic acid, and 10% palmitic acid was used in the UNIFAC calculation to model soybean oil.

FIG. 14C plots the $g^{mix}$ of water and soybean oil at 25° C. versus the mole fraction of water. Because the miscibility of two liquids requires both $$g^{mix} < 0 \text{ and } \left(\frac{\partial^2 g^{mix}}{\partial x^2}\right)_{T,P} > 0 \quad (6)$$

where T is temperature and P is pressure, a solution of water and soybean oil is stable in Regime I($x<x_t$), metastable in Regime II ($x_t<x<x_o$), and unstable in Regime III ($x>x_o$). To minimize the total free energy of the system, phase splitting into a pure water phase and a water-oil solution that has a water mole fraction of $x_t$ is very likely in Regime II and is guaranteed in Regime III. From this plot, water can dissolve in soybean oil up to 14 mole % ($x_t$) or 0.3 volume % while soybean oil can not dissolve in water, which agrees with the experimental observations.

The concentration of molecules, which dictates their frequency of interaction, is central to chemical and biological processes. This work exploits the high surface-area-to-volume ratio characteristic of the micro scale and demonstrates a flexible method to concentrate dissolved solutes and nanoparticles in aqueous microdroplets. By understanding the kinetics and the factors that affect droplet shrinkage, it should be possible to control precisely and dynamically the concentrations of dissolved species within individual droplets. In using droplets as nanoreactors for the chemical transformations of ultrasmall biological samples, this ability to concentrate the reactants will be especially critical because such samples are often present in minute amounts. This concentrating effect will only work for solutes that do not dissolve in or react with the organic phase, which is the case for many biological molecules, such as amino acids, DNAs, and many proteins and metabolites. Control over the precise concentrations of dissolved solutes within individual microdroplets can be broadly useful for studying molecular phenomena that are sensitive to concentrations, such as spatially confined chemical reactions, macromolecular crowding, and crystal formation.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A device comprising:
a substrate to contact a single biological cell;
means to remove a subcellular component of the biological cell;
a chemical reactant selected to facilitate detection of a molecular component present in the subcellular component removed from the biological cell;
a force generator to manipulate the at least one of the biological cell, the molecular component, and the subcellular component;
a separation microchannel on the substrate to separate the molecular component from the subcellular component; and
a controller, the controller comprising a processor and a memory logically coupled to the processor, the memory storing data and machine readable and executable instructions that when executed by the processor, cause a plurality of functions to be carried out, including using the force generator to encapsulate at least one of the subcellular component and the molecular component into an aqueous microdroplet.

2. The device of claim 1, further comprising a detector to identify or analyze the molecular component.

3. The device of claim 1, wherein the controller is further configured to implement the function of reducing a volume of the aqueous microdroplet to increase a relative concentration of the at least one of the subcellular component and the molecular component.

4. The device of claim 3, wherein said means to remove the subcellular component from the biological cell comprises a laser.

5. The device of claim 4, wherein the controller is further configured to implement the following functions:
using the force generator to generate a second microdroplet within a microfluidic channel, said second microdroplet encapsulating a chemical reactant; and
using the force generator to fuse the aqueous microdroplet encapsulating the at least one of the subcellular component and the molecular component with the second microdroplet, thereby exposing the at least one of the subcellular component and the molecular component to the chemical reactant.

6. The device of claim 1, further comprising:
a reactant droplet chamber configured to generate a microdroplet encapsulating the chemical reactant, the chemical reactant having been selected based on its ability to facilitate detection of the molecular component; and
a microfluidic channel on the substrate to receive the subcellular component.

7. The device of claim 4, wherein the laser is used in connection with at least one trap selected from the group consisting of an optical vortex trap, and an optical gradient trap.

8. The device of claim 7, further comprising a plurality of lasers for optical trapping and cell surgery.

9. The device of claim 1 wherein the substrate is a polymeric material.

10. The device of claim 9 wherein the substrate comprises at least one material selected from the group consisting of a polymeric material, polydimethylsiloxane (PDMS), polymethylmethacrylate (PMMA), polyester (PET), polytetrafluoroethylene (PTFE), polycarbonate, polyurethane, cyclic olefin copolymer, perfluoropolyether, polystyrene, polyvinylchloride, polyethyleneterephthalate glycol, and a combination thereof.

11. The device of claim 1 wherein the chemical reactant is a detectable marker.

12. The device of claim 11 wherein the detectable marker is based upon at least one labeling technique selected from the group consisting of immuno-labeling, immuno-magnetic labeling, quantum dot attachment, and labeling with a chemically reactive group.

13. The device of claim 11 wherein the detectable marker comprises at least one element selected from the group consisting of a reactive dye tag, a fluorescent tag, a non-fluorescent tag, and a contrast agent.

14. The device of claim 1 wherein the aqueous microdroplet is generated in an organic phase.

15. The device of claim 14 wherein the organic phase comprises at least one component selected from the group consisting of oil, soybean oil, mineral oil, n-hexadecane, decanol, nonanol, a perfluoro-based solution, perfluorononane, perfluorodecane, and acetophenone.

16. The device of claim 3 wherein the force comprises at least one force selected from the group consisting of a mechanical force, an electric field force, a magnetic field force, a hydrodynamic force, a surface tension force, an interfacial tension force, a thermal force, and a combination thereof.

17. The device of claim 1 wherein the chemical reactant is based upon at least one labeling technology selected from the group consisting of immuno-labeling, immuno-magnetic labeling, quantum dot attachment, and labeling with a chemically reactive group.

18. The device of claim 1 wherein the separation microchannel isolates the molecular component using at least one technique selected from the group consisting of liquid-liquid partition, precipitation, adsorption, chromatography, high-performance liquid chromatography, hydrophobic interaction chromatography, size-exclusion chromatography, protein affinity chromatography, hydroxyapatite chromatography, thiophilic chromatography, hydrophobic charge induction chromatography, immobilized boronic acid ligand chromatography, dye interaction chromatography, metal chelate affinity chromatography, immunoaffinity chromatography, ion-exchange chromatography, capillary electrophoresis, capillary zone electrophoresis, capillary isoelectric focusing, capillary gel electrophoresis, micellar electrokinetic capillary chromatography, and capillary electrochromatography.

19. The device of claim 2 wherein the detector comprises at least one device selected from the group consisting of a single-molecule confocal fluorescence microscope, and a mass spectrometer.

20. The device of claim 2 wherein the detector comprises at least one detection technology selected from the group consisting of immunoassay, enzyme-linked immunosorbant assay (ELISA), Western blot analysis, immunoligand assay, mass spectrometry, electrospray ionization mass spectrometry (ESI-MS), surface-enhanced laser desorption mass spectrometry (SELDI-MS), matrix-assisted laser desorption mass spectrometry (MALDI-MS), secondary ion mass spectrometry (SIMS), radiation-based spectroscopy, laser-induced fluorescence (LIF), two-photon excited fluorescence, surface-enhanced Raman spectroscopy, Fourier transform infrared spectroscopy (FTIR), electric field-based detection, alternating current impedance spectrometry, voltammetry, electrochemical detection, and conductivity measurement.

21. A system comprising:
a substrate to contact a single biological cell;
means to remove a subcellular component of the biological cell;
a reactant chamber configured to provide a chemical reactant selected to facilitate the detection of a molecular component present in the subcellular component removed from the biological cell;
a force generator to manipulate the at least one of the biological cell, the molecular component, and the subcellular component;
a separation microchannel on the substrate to separate the molecular component of the subcellular component;
a controller, the controller comprising a processor and a memory logically coupled to the processor, the memory storing data and machine readable and executable instructions that when executed by the processor, cause a plurality of functions to be carried out, including:
using a force generator to encapsulate at least one of the subcellular component and the molecular component into an aqueous microdroplet; and
reducing a volume of the aqueous microdroplet to increase a relative concentration of the at least one of the subcellular component and the molecular component.

22. The system of claim 21, further comprising a detector to analyze the molecular component.

23. The system of claim 21 wherein the force generator produces at least one force selected from the group consisting of a mechanical force, an electric field force, a magnetic field force, a hydrodynamic force, a surface tension force, an interfacial tension force, a thermal force, and a combination thereof.

24. The system of claim 21, further comprising a microfluidic channel on the substrate to receive the subcellular component.

25. The system of claim 21, wherein the chemical reactant is further selected to permeate a membrane of the cell.

26. The system of claim 21, wherein the laser is used in connection with at least one trap selected from the group consisting of an optical vortex trap, and an optical gradient trap.

27. The system of claim 21 wherein the substrate is a polymeric material.

28. The system of claim 27 wherein the substrate comprises at least one component selected from the group consisting of a polymeric material, polydimethylsiloxane (PDMS), polymethylmethacrylate (PMMA), polyester (PET), polytetrafluoroethylene (PTFE), polycarbonate, polyurethane, cyclic olefin copolymer, perfluoropolyether, polystyrene, polyvinylchloride, polyethyleneterephthalate glycol, and a combination thereof.

29. The system of claim 21, further comprising a plurality of lasers for optical trapping and cell surgery.

30. The system of claim 21, wherein the controller is further configured to control generation of the aqueous microdroplet and a size of the aqueous microdroplet.

31. The system of claim 21 wherein the chemical reactant is a detectable marker.

32. The system of claim 31 wherein the detectable marker is based on at least one labeling technology selected from the group consisting of immuno-labeling, immuno-magnetic labeling, quantum dot attachment, and labeling with a chemically reactive group.

33. The system of claim 31 wherein the detectable marker comprises at least one element selected from the group consisting of a reactive dye tag, a fluorescent tag, a non-fluorescent tag, and a contrast agent.

34. The system of claim 21 wherein the aqueous microdroplet is generated in an organic phase.

35. The system of claim 34 wherein the organic phase comprises at least one element selected from the group consisting of oil, soybean oil, mineral oil, n-hexadecane, decanol, nonanol, perfluoro-based solution, perfluorononane, perfluorodecane, and acetophenone.

36. A device comprising:
a substrate to contact a single biological cell;
means to selectively remove a portion of the single biological cell, the portion comprising a subcellular component of the biological cell that is transported across a cellular membrane of the single biological cell, while the single biological cell is disposed in a fluid volume defined by the substrate;
means to separate a molecular component from the subcellular component, while the subcellular component is disposed in a fluid volume defined by the substrate, where the molecular component is part of the subcellular component;
means to analyze the molecular component; and
a controller, the controller comprising a processor and a memory logically coupled to the processor, the memory storing data and machine readable and executable instructions that when executed by the processor, cause a plurality of functions to be carried out, including using a force generator to encapsulate at least one of the subcellular component and the molecular component into an aqueous microdroplet.

37. The device of claim 36, wherein the controller is further configured to implement the function of reducing the volume of the aqueous microdroplet by introducing the aqueous microdroplet into a fluid volume defined by the substrate, the fluid volume being filled with an organic liquid, and keeping the aqueous microdroplet in the organic liquid for a period of time sufficient to shrink the aqueous microdroplet by a desired amount, thereby increasing a relative concentration of the at least one of the subcellular component and the molecular component in the aqueous microdroplet.

38. The device of claim 1, wherein the controller is further configured to implement the function of reducing a volume of the aqueous microdroplet to increase a relative concentration of the at least one of the subcellular component and the molecular component by introducing the aqueous microdroplet into a volume filled with an organic liquid, and keeping the aqueous microdroplet in the organic liquid for a period of time sufficient to shrink the aqueous microdroplet by a desired amount, thereby increasing a relative concentration of the at least one of the subcellular component and the molecular component in the aqueous microdroplet.

39. The device of claim 36, further comprising at least one force generator to manipulate at least one of the subcellular component and a microdroplet, and the controller is further configured to implement the functions of:

introducing a detection marker into the biological cell, the detection marker marking at least one of the molecular component and the subcellular component; and using said means to selectively remove the portion of the single biological cell to remove the subcellular component from the biological cell after the detection marker has been introduced.

40. A device comprising:
a substrate configured to contact a single biological cell;
a separation microchannel on the substrate to separate the molecular component from the subcellular component; and
a controller, the controller comprising a processor and a memory logically coupled to the processor, the memory storing data and machine readable and executable instructions that when executed by the processor, cause a plurality of functions to be carried out, including using a force generator to encapsulate at least one of the subcellular component and the molecular component into an aqueous microdroplet.

41. The device of claim 40, wherein the controller is further configured to implement the function of reducing a volume of the aqueous microdroplet by introducing the aqueous microdroplet into a volume filled with an organic liquid, and keeping the aqueous microdroplet in the organic liquid for a period of time sufficient to shrink the aqueous microdroplet by a desired amount, thereby increasing a relative concentration of the at least one of the subcellular component and the molecular component in the aqueous microdroplet.

42. A system comprising:
a substrate configured to contact a single biological cell;
a reactant chamber configured to employ a chemical reactant selected to facilitate the detection of a molecular component present in a subcellular component removed from the biological cell;
a separation microchannel on the substrate to separate the molecular component from the subcellular component; and
a controller configured to implement the functions of:
using a force generator to encapsulate at least one of the subcellular component and the molecular component into an aqueous microdroplet; and
reducing a volume of the aqueous microdroplet to increase a relative concentration of the at least one of the subcellular component and the molecular component.

43. The system of claim 42, wherein the controller is further configured to implement the function of reducing a volume of the aqueous microdroplet by introducing the aqueous microdroplet into a volume filled with an organic liquid, and keeping the aqueous microdroplet in the organic liquid for a period of time sufficient to shrink the aqueous microdroplet by a desired amount, thereby increasing a relative concentration of the at least one of the subcellular component and the molecular component in the aqueous microdroplet.

44. A device comprising:
a substrate to contact a single biological cell;
means to remove a subcellular component of the biological cell;
means to separate a molecular component from the subcellular component;
means to analyze the molecular component;
means to encapsulate at least one component selected from a group of components consisting of the subcellular component and the molecular component into an aqueous microdroplet; and
means to reduce a volume of the aqueous microdroplet to increase a relative concentration of the at least one of the subcellular component and the molecular component in the aqueous microdroplet.

45. A device comprising:
a substrate to contact a single biological cell;
means to transport a subcellular component of the biological cell across a cellular membrane of the single biological cell, thus removing the subcellular component from the single biological cell, while the single biological cell is disposed in a fluid volume defined by the substrate;
means to separate a molecular component from the subcellular component, while the subcellular component is disposed in a fluid volume defined by the substrate, where the molecular component is part of the subcellular component;
means to encapsulate at least one component into an aqueous microdroplet, the at least one component being selected from a group of components consisting of the subcellular component and the molecular component, while the at least one component is disposed in a fluid volume defined by the substrate;
means to reduce a volume of the aqueous microdroplet to increase a relative concentration of the at least one of the subcellular component and the molecular component in the aqueous microdroplet; and
means to analyze the molecular component.

* * * * *